United States Patent
Henrich et al.

(10) Patent No.: US 8,784,847 B2
(45) Date of Patent: Jul. 22, 2014

(54) SYNTHESIS OF 1-AMINO-1,3,3,5,5,-CYCLOHEXANE MESYLATE

(75) Inventors: Markus Henrich, Munzenberg (DE); Simona Negura, Darmstadt (DE); Gergely Tasi, Budapest (HU); Pal Kocsan, Csopak (HU); Federico Sbrogio, Montecchio Maggiore (IT); Michael Pyerin, Brunn am Gebirge (AT); Herbert Koller, Vienna (AT)

(73) Assignee: Merz Pharma GmbH & Co. KGaA, Frankfurt am Main (DE)

( * ) Notice: Subject to any disclaimer, the term of this patent is extended or adjusted under 35 U.S.C. 154(b) by 0 days.

(21) Appl. No.: 13/138,883

(22) PCT Filed: Apr. 16, 2010

(86) PCT No.: PCT/EP2010/002361
§ 371 (c)(1), (2), (4) Date: Dec. 22, 2011

(87) PCT Pub. No.: WO2010/118889
PCT Pub. Date: Oct. 21, 2010

(65) Prior Publication Data
US 2012/0100184 A1   Apr. 26, 2012

Related U.S. Application Data

(60) Provisional application No. 61/214,015, filed on Apr. 17, 2009.

(30) Foreign Application Priority Data

Apr. 17, 2009 (EP) .................... 09005471

(51) Int. Cl.
*A61K 9/00* (2006.01)
(52) U.S. Cl.
USPC ......................... 424/400; 514/810
(58) Field of Classification Search
USPC ....................................... 424/400
See application file for complete search history.

(56) References Cited

U.S. PATENT DOCUMENTS

| | | | |
|---|---|---|---|
| 5,514,713 A * | 5/1996 | Nakai et al. | 514/533 |
| 7,019,140 B2 | 3/2006 | Cabri et al. | |
| 7,563,821 B2 | 7/2009 | Xiang et al. | |
| 7,829,521 B2 | 11/2010 | Antoine et al. | |
| 2006/0002999 A1 * | 1/2006 | Yang et al. | 424/464 |
| 2006/0198884 A1 * | 9/2006 | Yang et al. | 424/464 |
| 2008/0058369 A1 * | 3/2008 | Allen et al. | 514/303 |
| 2008/0194698 A1 | 8/2008 | Hermanussen et al. | |

FOREIGN PATENT DOCUMENTS

| | | |
|---|---|---|
| WO | 97/24118 | 7/1997 |
| WO | WO 97/24118 | 7/1997 |
| WO | 99/01416 | 1/1999 |
| WO | WO 99/01416 | 1/1999 |
| WO | 2006/094574 | 9/2006 |
| WO | WO 2006/094674 | 9/2006 |
| WO | WO 2007/062815 | 6/2007 |

OTHER PUBLICATIONS

Danysz et al (Amino-Alkyl-Cyclohexanes as a Novel Class of Uncompetitive NMDA Receptor Antagonists, 2002, Current Pharmaceutical Design, vol. 8, pp. 835-843).*
International Search Report for PCT/EP2010/002361 of Jul. 26, 2010.
Steffen Schweizer, Dissertation, Jan. 1, 2001, p. I-VII, 1, 188-192, 200-201, XP009136396.
Danysz et al., Aminoalkyl-cyclohexanes as a novel class of uncompetitive NMDA receptor antagonist, Current Pharmaceutical Design, 2002, 8, 835-843.
Extended European Search Report EESR of priority application EP 09 005 471.9, Feb. 2009.
Guidance for Industry, Department of Health and Human Services et al, Nov. 2003 Revision 1, Q3C-Tables and List.
International Preliminary Report on Patentability IPRP of PCT/EP2010/002361, 2010.
International Search Report ISR of PCT/EP2010/002361, Mar. 2010.
Jirgonsons et al., Synthesis and structure-affinity relationships of 1,3,5-alkylsubstituted cyclohexylamines binding at NMDA PCP site, European J. Med. Chem. 35 (2000), 555-565.
Schweizer, Erstellung eines Präformulierungskonzeptes für mittelständische Pharmaunternehmen unter besonderer Berücksichtigung der physikalisch-chemischen Eigenschaften neuer Arzneistoffe, dargestelit am Beispiel der NMDA-Antagonisten MRZ 2/579 und MRZ 2/576. Dissertation, Johann-Wolfgang-Goethe-University in Frankfurt/Main 2001.

* cited by examiner

*Primary Examiner* — Brian-Yong Kwon
*Assistant Examiner* — Mark V Stevens
(74) *Attorney, Agent, or Firm* — Hueschen and Sage

(57) ABSTRACT

Process for manufacturing 1-amino-1,3,3,5,5-pentamethylcyclohexane mesylate comprising step (i):
(i) reacting 1-amino-1,3,3,5,5-pentamethylcyclohexane with methane sulfonic acid in a solvent or a mixture of two or more solvents selected from anisole, cumene, pentane, hexane, heptane, isooctane, methyl acetate, propyl acetate, isopropyl acetate, n-butyl acetate, isobutyl acetate, methyl ethyl ketone, methyl isopropylketone, methyl isobutyl ketone, dimethyl sulphoxide, tetrahydrofuran, methyltetrahydrofuran, 1,1-diethoxypropane, 1,1-dimethoxymethane, and 2,2-dimethoxypropane.

24 Claims, 4 Drawing Sheets

SYNTHESIS OF 1-AMINO-1,3,3,5,5,-CYCLOHEXANE MESYLATE

FIELD OF THE INVENTION

The present invention relates to a process for manufacturing 1-amino-1,3,3,5,5-pentamethylcyclohexane (neramexane) mesylate comprising a step (i) of reacting 1-amino-1,3,3,5,5-pentamethylcyclohexane with methane sulfonic acid in a solvent or a mixture of two or more solvents.

BACKGROUND OF THE INVENTION

Neramexane and salts thereof are valuable agents for the continuous therapy of patients suffering from diseases and conditions such as tinnitus, Alzheimer's dementia and neuropathic pain.

WO 99/01416 discloses the preparation of neramexane, neramexane hydrochloride or intermediate products starting from isophorone.

Figure 1:
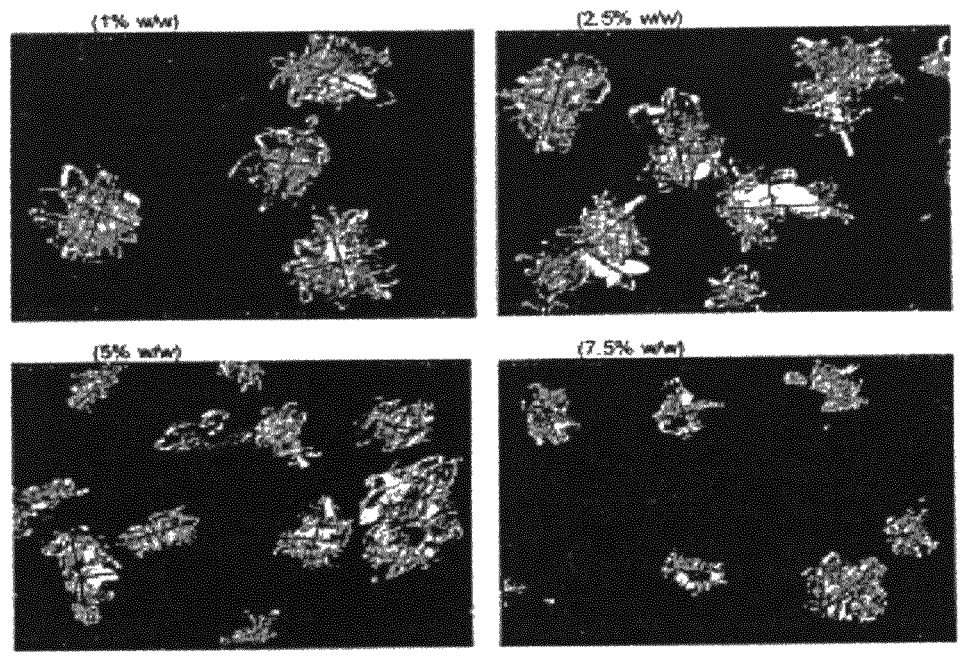

A further reaction scheme for the preparation of neramexane and neramexane hydrochloride also starting from isophorone is known from Danysz et al ("*Amino-alkyl-cyclohexanes as a novel class of uncompetitive NMDA receptor antagonist*", Current Pharmaceutical Design, 2002, 8, 835-843). FIG. 1 of said publication discloses the following reaction sequences:

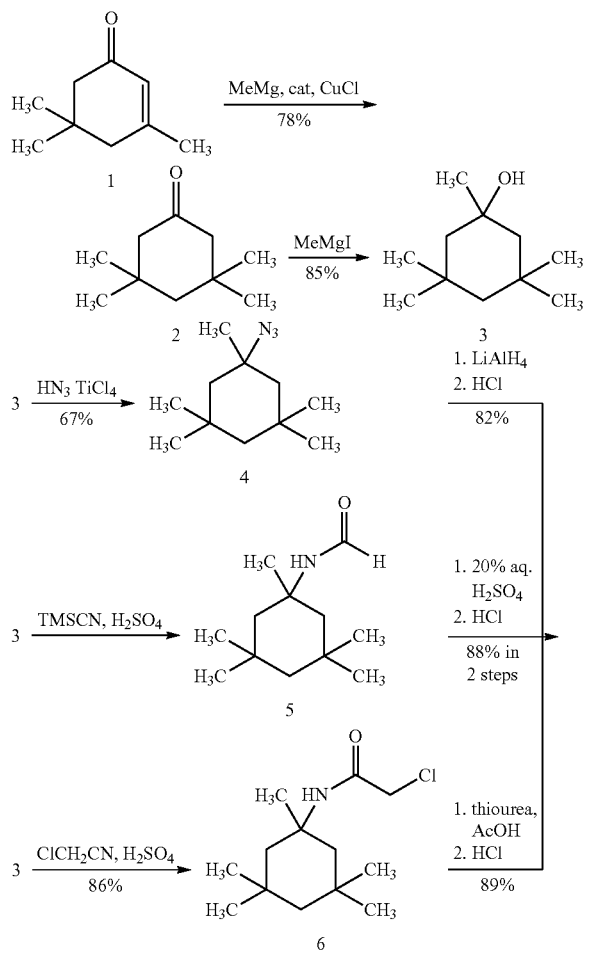

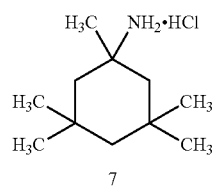

Another route for the preparation of neramexane and neramexane hydrochloride starting from isophorone is disclosed by Jirgensons et. al. in European J. Med. Chem. 35 (2000), 555-565 (*Synthesis and structure-affinity relationships of 1,3,5-alkylsubstituted cyclohexylamines binding at NMDA receptor PCP site*).

The addition salt of neramexane with methane sulfonic acid (the mesylate) is also known to be a potent drug for the above mentioned diseases (WO 2007/062815).

WO 99/01416 suggests to prepare the mesylate from the amino compound by acid addition according to conventional procedure, or neutralizing the hydrochloride resulting in the free base, and then re-acidifying the free base with methane sulfonic acid.

Schweizer (Erstellung eines Präformulierungskonzeptes für mittelständische Pharmunternehmen unter besonderer Berücksichtigung des physikalisch-chemischen Eigenschaften neuer Arzneistoffe, dargestellt am Beispiel der NMDA-Antagonisten MRZ 2/579 and MRZ 2/576, Dissertation, Johann-Wolfgang-Goethe-University in Frankfurt/Main, 2001) suggests a variety of solvents, in which neramexane mesylate may be re-crystallized. Suitable solvents are ethyl acetate, acetone, dichloromethane, water, diethyl ether, 1,4-dioxane, ethanol 70%, ethanol 96%, isopropanol, and toluene. Re-crystallization from acetone and dichloromethane may result in solvates. The solvent may be removed at elevated temperature leading to a destruction of the solvates.

OBJECTS OF THE INVENTION

It is an object of the present invention to establish a manufacturing method for neramexane mesylate (1-amino-1,3,3,5,5-pentamethylcyclohexane mesylate) that may be performed on an economical industrial scale resulting in a product that may be reliably used in medicinal applications. This method should provide neramexane mesylate in high yields and purity and in particle sizes and particle size distributions that may be varied depending upon need by adjusting the process parameters, such as choice of solvent and the way of isolating neramexane mesylate from the reaction mixture obtained in step (i).

SUMMARY OF THE INVENTION

The invention relates to a process for manufacturing 1-amino-1,3,3,5,5-pentamethylcyclohexane mesylate comprising step (i):
(i) reacting 1-amino-1,3,3,5,5-pentamethylcyclohexane with methane sulfonic acid in a solvent or a mixture of two or more solvents selected among anisole, cumene; pentane, hexane, heptane, isooctane; methyl acetate, propyl acetate, isopropyl acetate, n-butyl acetate, isobutyl acetate; methyl ethyl ketone, methyl isopropylketone, methyl isobutyl ketone; dimethyl sulphoxide; tetrahydrofurane, methyltetrahydrofurane, 1,1-diethoxypropane, 1,1-dimethoxymethane, and 2,2-dimethoxypropane.

In one embodiment, the solvent within step (i) is anisole, or a mixture of anisole with at least one of the other solvents defined above.

In another embodiment, the solvent within step (i) comprises water.

In one embodiment the solvent comprises from 0.1 to 10% by weight water based on the total amount of water and solvent, or from 0.1 to 8% by weight, or from 0.1 to 5% by weight, or from 0.1 to 4% by weight, or from 0.1 to 2% by weight, or from 0.1 to 1% by weight.

In another embodiment, the solvent within step (i) is selected from the group of tetrahydrofurane, 1,1-diethoxypropane, 1,1-dimethoxymethane, 2,2-dimethoxypropane; methyl ethyl ketone, methyl isopropylketone, and methyl isobutyl ketone; optionally together with water.

In one embodiment, the solvent within step (i) is selected from the group of tetrahydrofurane, 1,1-diethoxypropane, 1,1-dimethoxymethane, 2,2-dimethoxypropane; methyl ethyl ketone, methyl isopropylketone, and methyl isobutyl ketone; and comprises from 0.1 to 10% by weight water based on the total amount of water and solvent, or from 0.1 to 8% by weight, or from 0.1 to 5% by weight, or from 0.1 to 4% by weight, or from 0.1 to 2% by weight, or from 0.1 to 1% by weight.

In one embodiment, in said step (i), the ratio of the volume of solvent to the weight of 1-amino-1,3,3,5,5-pentamethylcyclohexane is from 5:1 to 50:1 (ml/g).

In one embodiment, the temperature within step (i) is from −20° C. to 120° C.

In one embodiment, the temperature within step (i) is from 0° C. to 60° C.

In one embodiment, the temperature within step (i) is from 0° C. to 60° C., and the solvent is selected from the group of anisole, cumene; pentane, hexane, heptane, isooctane; methyl ethyl ketone, methyl isopropyl ketone; methyl isobutyl ketone; tetrahydrofurane; and mixtures thereof; optionally together with water.

In one embodiment, the process according to the invention comprises step (ii):
(ii) isolating 1-amino-1,3,3,5,5-pentamethylcyclohexane mesylate from the reaction mixture of step (i) by crystallization.

In one embodiment, the crystallization in step (ii) is achieved by reducing the temperature of the reaction mixture of step (i), adding anti-solvents, or distilling off partially the solvent used in step (i), or a combination of two or more of these measures.

In one embodiment, in step (ii), the temperature is reduced to a temperature within the range of from −20° C. to 50° C.

In one embodiment, the process further comprises at least one of the steps (iii) to (v) subsequent to step (i) or step (ii):
(iii) re-crystallizing the product formed in step (i) or step (ii) from one or more of the solvents as defined above;
(iv) adding 1-amino-1,3,3,5,5-pentamethylcyclohexane mesylate in any one of the preceding steps (i) to (iii);
(v) de-agglomerating and/or milling the product formed in any one of the preceding steps (i) to (iv).

In one embodiment, in step (i) and/or step (iii), said solvent is selected from the group of anisole, cumene; methyl ethyl ketone, methyl isopropyl ketone, methyl isobutyl ketone; tetrahydrofurane; n-butylacetate; and mixtures thereof; optionally together with water; and wherein in step (i) and/or step (iii) the temperature is from 60° C. to 120° C.

In one embodiment, the process according to the invention further comprises steps (a) to (c) prior to step (i):

(a) converting isophorone to 3,3,5,5-tetramethylcyclohexanone;
(b) converting 3,3,5,5-tetramethylcyclohexanone to 1,3,3,5,5-pentamethylcyclohexanol;
(c) converting 1,3,3,5,5-pentamethylcyclohexanol to 1-amino-1,3,3,5,5-pentamethylcyclohexane.

In one embodiment, the process according to the invention further comprises a step (vii):
(vii) converting 1-amino-1,3,3,5,5-pentamethylcyclohexane mesylate obtained according to the process according to the invention to 1-amino-1,3,3,5,5-pentamethylcyclohexane.

In a further embodiment, the process according to the invention further comprises a step (viii):
(viii) converting the 1-amino-1,3,3,5,5-pentamethylcyclohexane obtained in step (vii) into a pharmaceutically acceptable salt or derivative of 1-amino-1,3,3,5,5-pentamethylcyclohexane, said salt being different from 1-amino-1,3,3,5,5-pentamethylcyclohexane mesylate.

In one aspect, the invention relates to 1-amino-1,3,3,5,5-pentamethylcyclohexane which is free from 1-amino-1,3,3-trans-5-tetramethylcyclohexane.

In another aspect, the invention relates to the use of anisole or a mixture of anisole and at least one of the solvents as defined within step (i) for the crystallization and/or re-crystallization of 1-amino-1,3,3,5,5-pentamethylcyclohexane mesylate.

In one aspect, the invention relates to 1-amino-1,3,3,5,5-pentamethylcyclohexane mesylate crystals, wherein the crystals are star-shaped.

In one aspect, the invention relates to 1-amino-1,3,3,5,5-pentamethylcyclohexane mesylate particles, wherein less than 20% by weight of the total particles have a particle size of 10 μm and less, or wherein less than 15% by weight of the particles have a particle size of 10 μm and less, or wherein less than 10% by weight of the particles have a particle size of 10 μm and less.

In one aspect, the invention relates to a process for producing a pharmaceutical composition comprising 1-amino-1,3,3,5,5-pentamethylcyclohexane mesylate crystals, wherein the crystals are star-shaped; or 1-amino-1,3,3,5,5-pentamethylcyclohexane mesylate particles, wherein less than 20% by weight of the total particles have a particle size of 10 μm and less, or wherein less than 15% by weight of the particles have a particle size of 10 μm and less, or wherein less than 10% by weight of the particles have a particle size of 10 μm and less; or 1-amino-1,3,3,5,5-pentamethylcyclohexane which is free from 1-amino-1,3,3-trans-5-tetramethylcyclohexane; and optionally one or more pharmaceutically acceptable excipients.

In a further aspect, the invention relates to a pharmaceutical composition comprising 1-amino-1,3,3,5,5-pentamethylcyclohexane mesylate crystals, wherein the crystals are star-shaped; or 1-amino-1,3,3,5,5-pentamethylcyclohexane mesylate particles, wherein less than 20% by weight of the total particles have a particle size of 10 μm and less, or wherein less than 15% by weight of the particles have a particle size of 10 μm and less, or wherein less than 10% by weight of the particles have a particle size of 10 μm and less; or 1-amino-1,3,3,5,5-pentamethylcyclohexane which is free from 1-amino-1,3,3-trans-5-tetramethylcyclohexane; and optionally one or more pharmaceutically acceptable excipients.

In a further aspect, the invention relates to 1-amino-1,3,3,5,5-pentamethylcyclohexane mesylate crystals, wherein the crystals are star-shaped, or 1-amino-1,3,3,5,5-pentamethylcyclohexane mesylate particles, wherein less than 20% by weight of the total particles have a particle size of 10 μm and less, or wherein less than 15% by weight of the particles have a particle size of 10 μm and less, or wherein less than 10% by weight of the particles have a particle size of 10 μm and less, or 1-amino-1,3,3,5,5-pentamethylcyclohexane which is free from 1-amino-1,3,3-trans-5-tetramethylcyclohexane, for use as a medicament.

In a further aspect, the invention relates to 1-amino-1,3,3,5,5-pentamethylcyclohexane mesylate crystals, wherein the crystals are star-shaped, or 1-amino-1,3,3,5,5-pentamethylcyclohexane mesylate particles, wherein less than 20% by weight of the total particles have a particle size of 10 μm and less, or wherein less than 15% by weight of the particles have a particle size of 10 μm and less, or wherein less than 10% by weight of the particles have a particle size of 10 μm and less, or 1-amino-1,3,3,5,5-pentamethylcyclohexane which is free from 1-amino-1,3,3-trans-5-tetramethylcyclohexane, for use in the treatment of tinnitus.

In a further aspect, the invention relates to the use of 1-amino-1,3,3,5,5-pentamethylcyclohexane mesylate crystals, wherein the crystals are star-shaped, or 1-amino-1,3,3,5,5-pentamethylcyclohexane mesylate particles, wherein less than 20% by weight of the total particles have a particle size of 10 μm and less, or wherein less than 15% by weight of the particles have a particle size of 10 μm and less, or wherein less than 10% by weight of the particles have a particle size of 10 μm and less, or 1-amino-1,3,3,5,5-pentamethylcyclohexane which is free from 1-amino-1,3,3-trans-5-tetramethylcyclohexane, for the manufacture of a pharmaceutical composition for the treatment of tinnitus.

In a further aspect, the invention relates to a method of treating tinnitus in a patient in need thereof, comprising administering to the patient an effective amount of 1-amino-1,3,3,5,5-pentamethylcyclohexane mesylate crystals, wherein the crystals are star-shaped, or 1-amino-1,3,3,5,5-pentamethylcyclohexane mesylate particles, wherein less than 20% by weight of the total particles have a particle size of 10 μm and less, or wherein less than 15% by weight of the particles have a particle size of 10 μm and less, or wherein less than 10% by weight of the particles have a particle size of 10 μm and less, or 1-amino-1,3,3,5,5-pentamethylcyclohexane which is free from 1-amino-1,3,3-trans-5-tetramethylcyclohexane.

In another aspect, the invention relates to a pharmaceutically acceptable salt that may be obtained according to step (viii).

In another aspect, the invention relates to a pharmaceutically acceptable salt that may be obtained according to step (viii) for use as a medicament.

In another aspect, the invention relates to a pharmaceutically acceptable salt that may be obtained according to step (viii) for use in the treatment of tinnitus.

In another aspect, the invention relates to the use of a pharmaceutically acceptable salt that may be obtained according to step (viii) for the manufacture of a pharmaceutical composition for the treatment of tinnitus.

In another aspect, the invention relates to a method of treating tinnitus in a patient in need thereof, comprising administering to the patient an effective amount of a pharmaceutically acceptable salt that may be obtained according to step (viii).

DETAILED DESCRIPTION OF THE INVENTION

The present invention relates to a process for manufacturing neramexane mesylate.

The term "neramexane mesylate" refers to 1-amino-1,3,3,5,5-pentamethylcyclohexane mesylate. The term also encompasses solvates, conjugates, prodrugs, polymorphic forms, and derivatives thereof.

The term "solvate" encompasses a product, wherein 1-amino-1,3,3,5,5-pentamethylcyclohexane mesylate is associated with molecules of a solvent, or attracts such molecules. If the solvent is water, the solvate is also termed as "hydrate".

In one embodiment, the term "solvate" comprises neramexane mesylate in which the solvent is incorporated on lattice sites of the crystal lattice of neramexane mesylate.

In another embodiment, the term "solvate" encompasses a product in which the solvent adheres to neramexane mesylate without being incorporated on lattice sites.

In one embodiment, the solvent may be removed from the solvate by the common methods, such as by applying elevated temperature and/or vacuum.

The term "conjugate" encompasses a product, wherein neramexane mesylate is covalently or non-covalently attached to a carrier.

The term "prodrug" encompasses a pharmacological substance derived from neramexane mesylate or a substance from which neramexane mesylate is prepared, and which is administered in an inactive or significantly less active form compared to neramexane itself.

The term "polymorphic form" encompasses neramexane mesylate crystallizing in different crystal structures.

The term "derivative thereof" encompasses neramexane mesylate wherein the amino group is derivatized with one or two alkyl groups.

Specifically, the present invention relates to a process for manufacturing 1-amino-1,3,3,5,5-pentamethylcyclohexane mesylate comprising the reaction of 1-amino-1,3,3,5,5-pentamethylcyclohexane with methane sulfonic acid.

More specifically, the present invention relates to a process for manufacturing 1-amino-1,3,3,5,5-pentamethylcyclohexane mesylate comprising at least step (i), and optionally steps (ii) to (v):

(i) reacting 1-amino-1,3,3,5,5-pentamethylcyclohexane with methane sulfonic acid in a solvent;
(ii) isolating 1-amino-1,3,3,5,5-pentamethylcyclohexane mesylate from the reaction mixture of step (i) by crystallization;
(iii) re-crystallizing the product formed in step (i) or step (ii);
(iv) adding 1-amino-1,3,3,5,5-pentamethylcyclohexane mesylate in any one of the preceding steps (i) to (iii);
(v) de-agglomerating and/or milling the product formed in any one of the preceding steps (i) to (iv).

Step (i)

In one embodiment, the solvent employed in step (i) is selected such that one or more of the following is achieved: allowing 1-amino-1,3,3,5,5-pentamethylcyclohexane mesylate to form crystals; allowing the control of particle size distribution of the formed 1-amino-1,3,3,5,5-pentamethylcyclohexane mesylate; allowing 1-amino-1,3,3,5,5-pentamethylcyclohexane mesylate to be formed in high purity and high yield; allowing for good removability of the solvent from the formed 1-amino-1,3,3,5,5-pentamethylcyclohexane mesylate; allowing for good stability of the solvent and 1-amino-1,3,3,5,5-pentamethylcyclohexane mesylate under the reaction conditions; allowing the solvent to perform in relatively small quantity; allowing the solvent to be safely applicable in view of technical realization of the process according to step (i); allowing the solvent to be pharmaceutically acceptable.

The term "pharmaceutically acceptable" in connection with the solvent means that said solvent does not affect the health of a human and/or is well-tolerated by a human.

In one embodiment, the solvent or a mixture of two or more solvents employed in step (i) is/are selected among anisole, cumene; methyl acetate, propyl acetate isopropyl acetate, n-butyl acetate, isobutyl acetate; dimethyl sulphoxide; pentane, hexane, heptane, isooctane; methyl ethyl ketone, methyl isobutyl ketone, methyl isopropyl ketone; tetrahydrofurane, 1,1-diethoxypropane, 1,1-dimethoxymethane, 2,2-dimethoxypropane, and methyltetrahydrofurane. Some of the solvents listed above are classified as "Class 3 solvents" according to the ICH guidelines "Guidance for Industry" issued by the US Department of Health and Human Services et al, November 2003 Revision 1 "Q3C—Tables and List".

In one embodiment, the solvent in step (i) is selected among anisole, and cumene.

In another embodiment, the solvent in step (i) is selected among pentane, hexane, heptane, and isooctane.

In another embodiment, the solvent in step (i) is dimethyl sulphoxide.

In another embodiment, the solvent in step (i) is selected among methyl ethyl ketone, methyl isopropyl ketone, and methyl isobutyl ketone.

In another embodiment, the solvent in step (i) is selected among tetrahydrofurane, methyltetrahydrofurane, 1,1-dimethoxymethane, 1,1-diethoxypropane, and 2,2-dimethoxypropane.

In another embodiment, the solvent in step (i) is selected from the group of methyl acetate, propyl acetate, isopropyl acetate, n-butyl acetate, and isobutyl acetate. In another embodiment, said acetates are not used as solvent due to their possible instability under acidic conditions, e.g. if the reaction according to step (i) is performed at elevated temperature.

If the target compound as formed in step (i) is isolated, e.g. by the common methods such as filtration or centrifugation and is optionally dried, it may contain residual solvent.

In one embodiment, the present invention pertains to 1-amino-1,3,3,5,5-pentamethylcyclohexane mesylate, as produced according to the process claimed herein, which contains 5% by weight or less, or 4% by weight or less, or 3% by weight or less, or 2% by weight or less, or 1.5% by weight or less, or 1% by weight or less residual solvent based on the total amount of mesylate and solvent.

In one embodiment, 1-amino-1,3,3,5,5-pentamethylcyclohexane mesylate contains 0.50% by weight or less residual solvent based on the total amount of mesylate and solvent. In a further embodiment, 1-amino-1,3,3,5,5-pentamethylcyclohexane mesylate contains 0.05% by weight or less residual solvent based on the total amount of mesylate and solvent.

Step (i) may be performed by controlling not only the solvent but at least one or more of the following: temperature, quantity of solvent with regard to employed 1-amino-1,3,3,5,5-pentamethylcyclohexane, water content of the selected solvent.

In one embodiment, the temperature within step (i) is from −20° C. to 120° C.

In one embodiment, the temperature within step (i) is between 50° C. and 100° C., or 50° C. to 90° C., or 50° C. and 80° C., or from 70° C. to 80° C., or is 80° C.

In one embodiment, the temperature within step (i) is from 0° C. to 60° C. In one embodiment, the temperature within step (i) is ambient temperature.

In one embodiment, the present invention pertains to a process as outlined above wherein in said step (i) the ratio of the volume of solvent to weight of 1-amino-1,3,3,5,5-pentamethylcyclohexane is from 5:1 to 50:1 (ml/g).

In one embodiment, the ratio of the volume of solvent to weight of 1-amino-1,3,3,5,5-pentamethylcyclohexane is from 5:1 to 20:1 (ml/g).

In another embodiment, the ratio of the volume of solvent to weight of 1-amino-1,3,3,5,5-pentamethylcyclohexane is from 5:1 to 10:1 (ml/g).

In another embodiment, the ratio of the volume of solvent to weight of 1-amino-1,3,3,5,5-pentamethylcyclohexane is from 5:1 to 8:1 (ml/g).

In one embodiment, said solvent employed in step (i) is selected from at least one of anisole, cumene, dimethyl sulphoxide, heptane, methyl ethyl ketone, methyl ethyl ketone in admixture with water, e.g. in an amount of water of 0.01 to 5% by weight, methyl i-butyl ketone, pentane, tetrahydrofurane and mixtures thereof.

Anisole as Solvent

The inventors have discovered that anisole may be advantageously used as solvent within the indicated temperature ranges and volume to weight ranges since it complies very well with the above mentioned requirements. It allows 1-amino-1,3,3,5,5-pentamethylcyclohexane mesylate to form crystals, allows the control of particle size distribution of the formed 1-amino-1,3,3,5,5-pentamethylcyclohexane mesylate, and allows 1-amino-1,3,3,5,5-pentamethylcyclohexane mesylate to be formed in high purity and high yield. Despite its relatively high boiling point of 154° C., it may be relatively easily removed from 1-amino-1,3,3,5,5-pentamethylcyclohexane mesylate by drying, if necessary at elevated temperature and/or by employing vacuum. Anisole is stable under the acidic reaction conditions and performs already in relatively small quantities. It is safely applicable in view of the technical realization of the process. Furthermore, anisole is classified as class 3 solvent.

According to one aspect of the invention, the solvent within step (i) is anisole, or a mixture of anisole with at least one of the other solvents as defined above.

In one embodiment according to said aspect, said solvent is anisole or a mixture of anisole and at least one of n-butyl acetate, cumene, dimethyl sulphoxide, heptane, i-butyl acetate, i-propyl acetate, methyl ethyl ketone, methyl i-butyl ketone, pentane, propyl acetate, tetrahydrofurane, 1,1-diethoxypropane, 1,1-dimethoxymethane, 2,2-dimethoxypropane, isooctane, isopropyl ether, methyl i-propyl ketone and methyltetrahydrofurane, optionally together with water.

In one embodiment, said mixture is a mixture of anisole and heptane.

In one embodiment, the solvent is anisole and step (i) is performed within a temperature of from 50° C. and 100° C., or 50° C. to 90° C., or 50° C. and 80° C., or from 70° C. to 80° C., or is 80° C.

In one embodiment, the quantity of anisole is selected such that the mesylate formed within step (i) in the indicated temperature range remains dissolved within the solvent and precipitates upon cooling. In general, 1-amino-1,3,3,5,5-pentamethylcyclohexane mesylate is produced in the form of crystals, which can be isolated as such, e.g. according to step (ii) as defined below, e.g. may be isolated by filtration or centrifugation.

In one embodiment, 5 to 15 ml anisole, or 8 to 12 ml anisole, or 10 ml anisole are used per gram 1-amino-1,3,3,5,5-pentamethylcyclohexane or 1-amino-1,3,3,5,5-pentamethylcyclohexane mesylate in step (i) (and/or step (iii)).

If necessary, the mixture as obtained in step (i) (and/or step (ii) and/or step (iii) if these steps are employed as defined below), may be cooled to room temperature or even below room temperature or ambient temperature employing a predetermined cooling rate prior to isolation, e.g. a cooling rate of from 0.05° C./min to 2° C./min or from 0.5° C. to 2° C., or from 0.8° C. to 2° C.

The target compound neramexane mesylate may be obtained in high yield and a high quality which, without further purification, e.g. according to a re-crystallization step (iii) as defined below, is already suitable for the further processing, e.g. the processing into a pharmaceutical composition.

Pentane, Hexane, Heptane, Isooctane; Methyl Ethyl Ketone, Methyl Isobutyl Ketone, Methyl Isopropyl Ketone; Tetrahydrofurane as Solvent; Optionally Together with Water;

According to another aspect of the invention, the solvent is selected from the group of pentane, hexane, heptane, isooctane; methyl ethyl ketone, methyl isobutyl ketone, methyl isopropyl ketone; tetrahydrofurane; optionally together with water; and mixtures thereof.

The term "pentane, hexane, heptane" also encompasses the respective isomers.

If step (i) is performed using one or more of said aforesaid solvents, depending on the reaction guidance, the target compound may be obtained in high yields and a high quality which, without further purification of the target compound, e.g. according to a re-crystallization step (iii) as defined below, is suitable for the further processing, e.g. the processing into a pharmaceutical composition.

In one embodiment, 1-amino-1,3,3,5,5-pentamethylcyclohexane mesylate is obtained by adding methane sulfonic acid to a mixture of 1-amino-1,3,3,5,5-pentamethylcyclohexane in one or more of the above defined solvents, i.e. pentane, hexane, heptane, isooctane; methyl ethyl ketone, methyl isobutyl ketone, methyl isopropyl ketone; tetrahydrofurane; optionally together with water; and mixtures thereof.

In one embodiment, the reaction according to step (i) is carried out in a temperature range of from 0° C. to 60° C. In one embodiment, the temperature within step (i) is ambient temperature, e.g. room temperature.

Commonly, 1-amino-1,3,3,5,5-pentamethylcyclohexane mesylate is insoluble or nearly insoluble in the aforesaid solvents and employing the above defined volume range of solvent to weight of 1-amino-1,3,3,5,5-pentamethylcyclohexane within said temperature range employed. Then, neramexane mesylate precipitates upon addition of the methane sulfonic acid to 1-amino-1,3,3,5,5-pentamethylcyclohexane.

In general, 1-amino-1,3,3,5,5-pentamethylcyclohexane mesylate is produced in the form of crystals, which can be isolated as such, e.g. according to step (ii) as defined below, e.g. may be isolated by filtration or centrifugation. Depending on the solvent, minor amounts of amorphous material may be produced, too. However, the degree of crystallinity is commonly sufficient to allow for X-ray diffraction analysis.

If necessary, the mixture as obtained in step (i) (and/or step (ii) and/or step (iii) if these steps are employed as defined below), may be cooled to room temperature or even below room temperature or ambient temperature employing a cooling rate prior to isolation, e.g. a cooling rate of from 0.05° C./min to 2° C./min or from 0.5° C. to 2° C., or from 0.8° C. to 2° C. The target compound commonly has a purity which renders it suitable for the further processing, e.g. into a pharmaceutical composition.

In one embodiment, the crystal size may be controlled by the reaction temperature in step (i).

In general, crystals which are produced in the upper range of the addressed temperature range of 0° C. to 60° C. such as between 50 and 55° C., are substantially larger than crystals, which are formed at lower temperature, e.g. at about 0° C., or between 0° C. and 20° C. This may be determined according to the known microscopic methods.

Mostly, the product formed at the lower temperature range is powdery having a low to medium bulk density, whereas the product formed at the upper temperature, i.e. between 50° C. to 60° C. or 50° C. to 55° C. range, is mostly crystalline having a high bulk density.

In a specific embodiment, 1-amino-1,3,3,5,5-pentamethylcyclohexane is dissolved in methyl ethyl ketone for performing step (i).

In one embodiment, 1-amino-1,3,3,5,5-pentamethylcyclohexane is dissolved in methyl ethyl ketone and the mixture is heated to a temperature of from 50 to 55° C. Then, methane sulfonic acid is added to the mixture, wherein the salts starts precipitating in the form of crystalline material. The mixture may be stirred and cooled down to a temperature of from 20 to 25° C., or from 0 to 5° C. The precipitated crystals may be isolated by filtration, or by centrifugation.

In another embodiment, 1-amino-1,3,3,5,5-pentamethylcyclohexane is dissolved in methyl ethyl ketone and methane sulfonic acid is added to the mixture, wherein the salts starts precipitating in the form of crystalline material. The precipitated crystals may be isolated by filtration, or by centrifugation, e.g. by filtration or centrifugation at ambient temperature.

In another embodiment, a solvent such as anisole or cumene may also be employed under analogous conditions as afore-mentioned, i.e. in a temperature range of from 0° C. to 60° C. In one embodiment, the temperature is ambient temperature.

Water-Comprising Solvents

According to another aspect of the invention, the solvent within (i) comprises water.

In one embodiment, the used solvent comprises water dissolved therein.

In one embodiment, the solvent and water are miscible.

The term "miscible" encompasses a mixture of said solvent and water, wherein solvent and water do not form separate layers but form a homogeneous phase.

The inventors have unexpectedly discovered that such a mixture comprising water may support the crystal formation in the process according to the invention, thus may support isolation step (ii) as discussed below, which is performed by crystallization.

Crystal formation may qualitatively determined by microscopical methods, or by X-ray diffraction analysis of the produced material.

In one embodiment, said mixture is selected from a solvent as used in the process according to the invention, which has a low solubility for 1-amino-1,3,3,5,5-pentamethylcyclohexane mesylate, but is miscible with water.

In one embodiment, the solvent in (i) is selected from a group of tetrahydrofurane, 1,1-diethoxypropane, 1,1-dimethoxymethane, 2,2-dimethoxypropane; methyl ethyl ketone, methyl isopropyl ketone, and methyl isobutyl ketone; and comprises water dissolved therein.

In another embodiment, the solvent is selected from the group of tetrahydrofurane, methyl ethyl ketone, methyl isopropylketone, and methyl isobutyl ketone; and comprises water dissolved therein.

In another embodiment, the solvent is selected from the group of tetrahydrofurane, and methyl ethyl ketone; and comprises water dissolved therein.

In one embodiment, the amount of water in the mixture of solvent and water is from 0.1 to 5% by weight, or from 0.1 to 3% by weight or from 0.5 to 3% by weight, or from 0.5 to 2.5% by weight, or from 1 to 2% by weight, based on the total amount of water and solvent.

In one embodiment, the solvent comprises from 0.1 to 10% by weight water based on the total amount of water and solvent, or from 0.1 to 8% by weight, or from 0.1 to 5% by weight, or from 0.1 to 4% by weight, or from 0.1 to 2% by weight, or from 0.1 to 1% by weight, based on the total amount of water and solvent.

In a specific embodiment, the solvent is methyl ethyl ketone in admixture with an amount of water of 0.01 to 5% by weight, wherein the reaction according to step (i) is carried out optionally in the presence of neramexane mesylate seeds according to a step (iv) as discussed in detail below. These seeds may be added prior to, together with, or after the addition of methane sulfonic acid to the mixture of neramexane and solvent. If necessary, the formed mesylate may be subjected to a milling or de-agglomerating step according to step (v) as defined below.

Addition of Methane Sulfonic Acid within Step (i)

In one embodiment of the process according to the invention, methane sulfonic acid is added to the solvent of step (i).

In one embodiment, 1-amino-1,3,3,5,5-pentamethylcyclohexane is dissolved or dispersed or suspended or emulsified in a solvent or a mixture of two or more of said solvents as defined above. Subsequent to the dissolving or dispersing or suspending or emulsifying, methane sulfonic acid is added in order to allow for the formation of the mesylate.

In one embodiment, methane sulfonic acid is added in the form of a solution of said acid in said solvent or a mixture of two or more of said solvents, wherein the solvent or the mixture of two or more of said solvents for said 1-amino-1,3,3,5,5-pentamethylcyclohexane and the solvent or the mixture of two or more of said solvents for said methane sulfonic acid may be independently selected from each other.

In one embodiment, the solvent for 1-amino-1,3,3,5,5-pentamethylcyclohexane and the solvent for methane sulfonic acid is or comprises anisole.

In one embodiment, methane sulfonic acid is added in neat form to 1-amino-1,3,3,5,5-pentamethylcyclohexane and the solvent, i.e. without dissolving or emulsifying the acid in a solvent.

In another embodiment, 1-amino-1,3,3,5,5-pentamethylcyclohexane, optionally dissolved or dispersed or suspended or emulsified in a solvent, is added to methane sulfonic acid, which optionally may be dissolved or emulsified in a solvent.

In another embodiment, 1-amino-1,3,3,5,5-pentamethylcyclohexane, optionally dissolved or dispersed or suspended or emulsified in a solvent, and methane sulfonic acid, optionally dissolved or emulsified in a solvent, are simultaneously but separately from each other added to a solvent employed in step (i).

Step (ii)

According to one embodiment, the invention refers to a process, wherein the 1-amino-1,3,3,5,5-pentamethylcyclohexane mesylate is isolated from the reaction mixture of step (i) by a step (ii) of crystallization.

The term "isolated from the reaction mixture of step (i) by a step (ii) of crystallization" encompasses a step, wherein the formed crystals are isolated by filtration or centrifugation.

Crystallization according to step (ii) may be achieved by reducing the temperature of the reaction mixture of step (i), adding anti-solvents or distilling off partially the solvent used in step (i), or a combination of two or more of these measures.

The term "anti-solvent" encompasses any solvent that, when added to the addition salt formed in step (i), results in the precipitation or the crystallization of the mesylate.

In order to achieve crystallization, in one embodiment, temperature may be reduced to an end temperature within the range of −20° C. to 50° C. In one embodiment the end temperature of crystallization is between 5° C. to 15° C. In one further embodiment the end temperature of crystallization is 20° C. In another embodiment the end temperature of crystallization is 10° C.

In one embodiment of the present invention, the time of stirring at the end temperature of crystallization is 3 hours or less, e.g. from 10 minutes to 2 hours.

Step (iii)

According to another embodiment of the invention, a solvent or a mixture of solvents is/are used, in which not only reaction step (i) and/or crystallization step (ii) may be performed, but which allow for re-crystallization such as a re-crystallization step (iii):

(iii) re-crystallizing the product formed in step (i) or step (ii) from one or more of the solvents used in step (i).

The term "re-crystallization" defines a process, wherein at least the majority, i.e. more than 50% by weight of the produced mesylate, is in a dissolved condition within the solvent, and precipitates if e.g. the temperature is decreased, or if an anti-solvent is added.

Of particular interest is a re-crystallization step according to step (iii), in which only a relatively small quantity of solvent is necessary, however, which nevertheless is suitable to highly purify the product and at the same time results in a high yield of re-crystallized and purified product, i.e. only relatively small quantities of product remain in the mother liquor. Such solvent is particularly interesting for the technical realization of the process due to economic reasons and for product properties due to quality and suitability as a pharmaceutically acceptable salt.

The term "pharmaceutically acceptable salt" in connection with neramexane mesylate means that said salt does not affect the health of a human and/or is well-tolerated by a human after administration.

In one embodiment, the solvents used in reaction step (i) and re-crystallization step (iii) are the same.

In one embodiment, it is not necessary to isolate mesylate formed in reaction step (i), e.g. to isolate mesylate according to crystallization step (ii). In one embodiment, at first reaction step (i) is performed and subsequently re-crystallization step (iii), e.g. by increasing the initial reaction temperature employed in step (i). In another embodiment, re-crystallization step (iii) may be performed together with reaction step (i), i.e. both steps are performed simultaneously, i.e. step (i) is performed at a temperature where re-crystallization occurs.

In another embodiment, mesylate formed in reaction step (i) is isolated, e.g. is isolated according to crystallization step (ii). Subsequent to the isolation, the mesylate is subjected to re-crystallization step (iii) employing the same solvent as used in step (i).

In another embodiment, the solvents used in reaction step (i) and re-crystallization step (iii) are different from each other. This means that mesylate formed in step (i) is isolated, e.g. is isolated according to step (ii). Subsequent to the isolation, it is subjected to step (iii) employing a solvent which is different from the solvent used in step (i).

Anisole as Solvent

The inventors have discovered that anisole complies with the aforesaid requirements.

Accordingly, in one embodiment, the invention relates to a process for the manufacture of 1-amino-1,3,3,5,5-pentamethylcyclohexane mesylate comprising step (i):

(i) reacting 1-amino-1,3,3,5,5-pentamethylcyclohexane with methane sulfonic acid in a solvent, wherein the solvent is anisole.

In one embodiment, the process comprises besides the above mentioned step (ii) a further step (iii):

(iii) re-crystallizing the product formed in step (i) or step (ii) in anisole.

In one embodiment, for step (i) and/or step (iii), 5 to 15 ml anisole, or 8 to 12 ml anisole are used, or 10 ml are used per gram 1-amino-1,3,3,5,5-pentamethylcyclohexane or 1-amino-1,3,3,5,5-pentamethylcyclohexane mesylate.

In one embodiment, step (i) and/or step (iii) are performed at a temperature range of from 60° C. to 120° C., or 60° C. to 100° C., or 70° C. to 100° C., or 80° C. to 100° C.

In one embodiment, for step (i) and/or step (iii), 5 to 15 ml anisole, or 8 to 12 ml anisole, or 10 ml anisole are used per gram 1-amino-1,3,3,5,5-pentamethylcyclohexane or the mesylate thereof, and step (i) and/or step (ii) are performed in a temperature range of from 60° C. to 100° C., or 80° C. to 100° C.

In one embodiment, for step (i) and/or step (iii), 8 to 12 ml anisole, or 10 ml anisole are used per gram 1-amino-1,3,3,5,5-pentamethylcyclohexane or the mesylate thereof, and step (i) and/or step (iii) are performed in a temperature range of from 80° C. to 100° C.

In one embodiment, steps (i) and (iii) are performed simultaneously.

In one embodiment, the required amounts of anisole and 1-amino-1,3,3,5,5-pentamethylcyclohexane are heated up to a temperature of approximately 80° C. to 90° C. Then, methane sulfonic acid is added, optionally diluted with anisole. In one embodiment, the required amounts of anisole and 1-amino-1,3,3,5,5-pentamethylcyclohexane are selected such that the formed mesylate remains dissolved in the mentioned temperature range. Commonly, the formed mesylate starts precipitating below a temperature of 80° C.

In one embodiment, the cooling rate as defined above may be employed for cooling the mixture obtained in step (iii), i.e. a cooling rate of from 0.05° C./min to 2° C./min, or from 0.5° C. to 2° C., or from 0.8° C. to 2° C.

In one embodiment, steps (i) and step (iii) are performed independently from each other. In one embodiment, step (i) and step (iii) are performed consecutively. Herein, step (i) is performed as defined above. The product may be isolated according to step (ii). The thus isolated product is then subjected to step (iii).

In one embodiment, product formed in step (i) is isolated, e.g. by filtration or centrifugation. Subsequently, the isolated product is subjected to step (iii) in a manner as described above. In one embodiment, it is mixed with anisole in an amount sufficient to dissolve the product formed in step (i) at a temperature between 80 to 100° C., or 90 to 100° C. Upon cooling down the solution, wherein the cooling rates as defined above may be employed, the product starts precipitating in the form of crystals.

Step (iii) may be performed once or several times in order to obtain a highly purified product, if necessary.

Commonly, in said crystallization and/or re-crystallization steps (ii) and/or (iii) crystals are obtained which are columnar. The term "lath-like" is synonymously used for columnar.

In one embodiment, if the initial temperature employed in step (i) is reduced to the above addressed end temperature in order to e.g. perform crystallization according to step (ii), or re-crystallization according to step (iii), the time of decreasing the temperature, i.e. the cooling rate, may be controlled. Via such control, the size of the formed particles and the particle size distribution may be controlled and adjusted.

In one embodiment, the reaction mixture obtained in step (i) and/or step (iii) which comprises dissolved or precipitating or precipitated mesylate is cooled down to an end temperature of from 40° C. to −10° C., or from 30° C. to −10° C., or from 20 to 0° C., wherein a cooling rate of from 0.05° C./min to 2° C./min or from 0.5° C. to 2° C., or 0.8° C. to 2° C. is employed.

In one embodiment, by applying such defined cooling rate, it is possible to control and adapt the particle size distribution.

In another embodiment, the reaction mixture obtained within step (i) is stirred upon cooling down the same.

In one embodiment, according to the commonly employed industrial production reactors, stirring rates between 5 to 75 rpm are employed. In one embodiment, a stirring rate of from 70 to 75 rpm, or from 45 to 55 rpm is employed.

In one embodiment, it is possible to control and to adjust the particle size distribution by means of the stirring rate.

In another embodiment, it is possible to control and to adjust the particle size distribution by means of the stirring rate and the cooling rate.

According to another aspect, some of the other solvents as defined above may be used for re-crystallization (iii). Said solvents may exhibit dissolving properties for neramexane mesylate which are different from the dissolving properties of anisole. This may e.g. be of interest with regard to re-crystallization in step (iii). Some of said solvents require relatively large amounts to perform re-crystallization, whereas others may already perform in relatively low amounts. The latter may be advantageous in view of an economic space/time yield. In particular anisole is a solvent which advantageously complies with an economic space/time yield.

Tetrahydrofurane; Cumene; Methyl Ethyl Ketone, Methyl Isopropyl Ketone, Methyl Isobutyl Ketone; or N-Butyl Acetate as Solvent; Optionally Together with Water In another embodiment, the solvent for re-crystallization according to step (iii) is selected from the group of tetrahydrofurane; cumene; methyl ethyl ketone, methyl isopropyl ketone and methyl isobutyl ketone; and n-butyl acetate; optionally together with water.

Commonly, as compared to anisole, a larger quantity of solvent is necessary in order to perform step (iii).

In one embodiment, the solvent for re-crystallization according to step (iii) is selected from the group of cumene; methyl ethyl ketone, methyl isopropyl ketone, and methyl isobutyl ketone; optionally together with water.

In one embodiment, about 20 ml tetrahydrofurane per gram neramexane mesylate are used to dissolve neramexane mesylate at a temperature of about 60° C.

In one embodiment, about 20 ml cumene per gram neramexane mesylate are used to dissolve neramexane mesylate at a temperature of about 104° C.

In one embodiment, about 20 ml methyl ethyl ketone per gram neramexane mesylate are used to dissolve neramexane mesylate at a temperature of about 80° C.

In one embodiment, about 20 ml methyl isobutyl ketone per gram neramexane mesylate are used to dissolve neramexane mesylate at a temperature of about 104° C.

In one embodiment, about 23 ml n-butyl acetate per gram neramexane mesylate are used to dissolve neramexane mesylate at a temperature of about 100° C.

In one embodiment, said solvent used for re-crystallization step (iii) is selected from the group of anisole, cumene; methyl ethyl ketone, methyl isopropyl ketone, methyl isobutyl ketone; tetrahydrofurane; and mixtures thereof; optionally together with water; and wherein in step (i) and/or step (iii) the temperature is from 60° C. to 120° C.

In one embodiment, said solvent is selected from the group of anisole, cumene; methyl ethyl ketone, methyl isopropyl ketone; methyl isobutyl ketone; tetrahydrofurane; and mixtures thereof; optionally together with water; and wherein in step (i) and/or step (iii) the temperature is from 60° C. to 120° C.; wherein in step (i) and/or step (iii), 5 to 30 ml solvent, or 8 to 25 ml solvent are used, per gram 1-amino-1,3,3,5,5-pentamethylcyclohexane or 1-amino-1,3,3,5,5-pentamethyl-cyclohexane mesylate.

In one embodiment, the reaction mixture as produced in step (i) and/or within re-crystallization step (iii), is only temporarily kept at a temperature of from 60° C. to 120° C. The term "temporarily" means that the reaction mixture is kept at a defined temperature or a defined temperature range for a defined period, such as 5 min to 120 min, or 10 min to 90 min, or 20 min to 60 min.

Upon cooling down the solutions, e.g. cooling down to ambient temperature, e.g. to room temperature, crystallized and/or re-crystallized neramexane mesylate is obtained.

Step (iv)

According to another embodiment of the invention, in order to support the crystallization according to step (ii) or re-crystallization according to step (iii), i.e. in order to avoid the formation of amorphous material as far as possible, which might negatively affect material properties of neramexane mesylate, already synthesized neramexane mesylate is added in step (i) and/or step (ii) and/or step (iii) in the form of neramexane mesylate seeds. Thus, in this embodiment, seeds of neramexane mesylate are added.

The term "neramexane mesylate seeds" encompasses neramexane mesylate in the form of powder or crystals.

In one embodiment, said seeds have a particle size distribution d(90) in the range of from 100 μm to 500 μm, or 100 μm to 400 μm, or 100 μm to 300 μm, or 150 μm to 300 μm, or 200 μm to 275 μm, or 200 μm to 250 μm as measured with laser diffraction as is known in the art.

In one embodiment, the amount of seeds is from 0.1% by weight to 10% by weight, or from 1 to 8% by weight based on the theoretical amount of neramexane mesylate to be formed in any one of steps (i) to (iii) (weight/weight).

According to one embodiment of the invention, the seeds are added to 1-amino-1,3,3,5,5-pentamethylcyclohexane mesylate, which is dissolved in anisole at a temperature between 80 to 100° C.

The inventors have unexpectedly discovered that upon cooling down such a seeded solution, wherein the solvent is anisole, 1-amino-1,3,3,5,5-pentamethylcyclohexane mesylate is obtained in a crystal habit which is different from the crystal habit as disclosed in the prior art, or to the crystal habit as obtained without seeding the mixture in step (i) and/or step (ii) and/or step (iii).

Contrary to the crystals as described in the prior art, e.g. crystals in the form of columnar or planar or isometric crystals, the crystals obtained according to said aspect of the invention, are star-shaped. This crystal habit obtained in anisole using seeds is unexpected.

The term "shape of stars" or "star-shaped" defines a crystal having a centre body or a core body from which crystalline material protrudes. The crystal has at least three protrusions or four protrusions or even more protrusions. The crystal may have multiple protrusions.

The term "obtained crystals have the shape of stars" encompasses crystals obtained in step (iii), wherein the majority of the crystals, i.e. more than 50% have said crystal form. The form and the estimation of the amount of formed crystals can be determined e.g. with microscopical methods, which are known in the art.

It is believed that said crystals may provide for a good flowability and processability into the common galenical forms of pharmaceutical compositions.

Accordingly, in one embodiment, the process comprises step (iv):
(iv) adding 1-amino-1,3,3,5,5-pentamethylcyclohexane mesylate to step (i) and/or step (ii) and/or step (iii), wherein the solvent is anisole.

As described above, the formed crystals may be isolated by filtration or centrifugation.

The obtained crystals, either formed in step (i) and/or step (ii) and/or step (iii) and/or step (iv) may be dried according to the known methods, e.g. in vacuum and/or at elevated temperature.

Some of the other solvents as used in the process according to the invention also provide star-shaped crystals if used in step (iii). Suitable solvents are e.g. cumene, methyl ethyl ketone, methyl isobutyl ketone, n-butyl acetate; optionally together with water.

In one embodiment, seeds are added at a temperature of from 60 to 120° C. according to step (iv) employing solvents such as cumene, methyl ethyl ketone, methyl isobutyl ketone, n-butyl acetate; optionally together with water.

The prior art (Schweizer) discloses for the re-crystallization from toluene crystals in the form of needles, or columnar crystals, or planar crystals. It has been surprisingly found that star-shaped crystals are formed, if toluene is used as solvent in at least step (iii) and step (iv) according to the method of the invention.

In one embodiment, the obtained crystals have a particle size distribution as defined below, which allows a tabletting without employing an additional milling step. This is advantageous in view of an industrial process.

Particle Size Distribution (PSD) of Neramexane Mesylate

According to another aspect, 1-amino-1,3,3,5,5-pentamethylcyclohexane mesylate as formed in the process according to the invention, is produced in the form of crystals having a particle size distribution of d(90) in the range of from 100 μm to 500 μm, or 100 μm to 400 μm, or 100 μm to 300 μm, or 150 μm to 300 μm, or 200 μm to 275 μm, or 200 μm to 250 μm as measured with laser diffraction as is known in the art.

In one embodiment, the particle size distribution is mono-modal.

In another embodiment, the particle size distribution is mono-modal having a shoulder in the region of low-sized particles.

In one embodiment, 1-amino-1,3,3,5,5-pentamethylcyclohexane mesylate in the form of crystals has a particle size distribution of d(90) in the range of 200 μm to 300 μm and 10% or less of the particles have a particle size of 55 μm or less, e.g. 5 μm or less.

In one embodiment, 1-amino-1,3,3,5,5-pentamethylcyclohexane mesylate in the form of crystals has a particle size distribution of d(90) in the range of 200 μm to 300 μm and 10% or less of the particles have a particle size of 5 μm or less; or 1-amino-1,3,3,5,5-pentamethylcyclohexane mesylate in the form of crystals has a particle size distribution of d(90) in the range of 200 μm to 400 μm and 10% or less of the particles have a particle size of 5 μm or less.

The particle size range of the resulting crystals is or may be sufficient that further milling of the crystals prior to pressing them to a tablet is not necessary. It is, however, well within the ambit of the present invention to mill or sieve the particles as obtained from the process as claimed herein.

In one embodiment of the present invention, anisole is used as the solvent and the crystallization according to step (ii) and/or re-crystallization according to step (iii) is carried out in such a manner that the neramexane mesylate is obtained in particle sizes that allow direct tabletting, i.e. they are obtained such that milling or sieving is not necessary.

In one embodiment of the present invention, anisole is used as the solvent and a seeding step according to step (iv) is carried out in addition to crystallization step (ii) and/or re-crystallization step (iii) in order to obtain the neramexane mesylate in particle sizes as defined above, which allow for direct tabletting, i.e. they are obtained such that milling or sieving is not necessary.

In this respect, it is noteworthy that crystals having particle sizes of more than 500 µm can often only be directly pressed to a pharmaceutical composition such as a tablet form under difficulties, since they are relatively coarse and hard and render the tablet inhomogeneous. Prior to the pressing, such coarse and hard crystals may have to be broken by appropriate means known in the art.

As is known from the prior art (Schweizer, Dissertation, page 200), approximately 20% by weight of the particle population of the mesylate disclosed therein has a diameter of less than 10 µm. Schweizer reports that said particulate matter has a better sorption of water vapour due to the relatively large surface of the particles than larger particles. However, said sorption of water vapour is disadvantageous and should be avoided for pharmaceutical compositions.

The inventors have unexpectedly discovered that 1-amino-1,3,3,5,5-pentamethylcyclohexane mesylate produced according to the process of the invention commonly has a lower amount of particulate matter as compared to the mesylate of the prior art.

The term "particulate matter" encompasses 1-amino-1,3,3,5,5-pentamethylcyclohexane mesylate particles having a diameter of 10 µm and less.

In one embodiment, less than 20% by weight of the total particles or particle population have a diameter of 10 µm and less, or less than 15% by weight have a diameter of 10 µm and less, or even less than 10% by weight have a diameter of 10 µm and less.

The particle size is determined according to the known methods employing laser diffraction as already mentioned above, and determining the distribution modal sizes.

Thus, 1-amino-1,3,3,5,5-pentamethylcyclohexane mesylate as produced according to the process of the present invention by employing the solvents defined therein has, due to its considerably lower amount of particulate matter, an advantageously reduced sorption of water vapour as compared to 1-amino-1,3,3,5,5-pentamethylcyclohexane mesylate known from the prior art.

Accordingly, in one aspect, the invention relates to 1-amino-1,3,3,5,5-pentamethylcyclohexane mesylate particles, wherein less than 20% by weight of the total particles have a diameter of 10 µm and less, or less than 15% by weight have a diameter of 10 µm and less, or less than 10% by weight have a diameter of 10 µm and less.

In view of an economic industrial process with e.g. regard to yield of target compound, which should be as high as possible, the product obtained according to reaction step (i) and/or crystallization step (ii) and/or re-crystallization step (iii) and/or seeding step (iv) is not subjected to a step of removing particulate matter from the product, e.g. removing particulate matter by a step of sieving.

Accordingly, in one aspect, the invention relates to 1-amino-1,3,3,5,5-pentamethylcyclohexane mesylate particles, wherein less than 20% by weight of the total particles or the particle population have a diameter of 10 µm and less, or less than 15% by weight have a diameter of 10 µm and less, or less than 10% by weight have a diameter of 10 µm and less; and wherein the 1-amino-1,3,3,5,5-pentamethylcyclohexane mesylate particles or the particle population are not subjected to a step of removing particulate matter.

In one embodiment, the referenced distribution modal size is achieved by employing anisole as a solvent.

In one embodiment employing anisole as a solvent, the particle size distribution of d(90) is in the range of from 100 µm to 500 µm, or from 200 µm to 400 µm.

In another embodiment, the particle size distribution of d(90) is in the range of from 100 µm to 500 µm, and less than 20% by weight of the total particles have a diameter of 10 µm and less, or less than 15% by weight have a diameter of 10 µm and less, or less than 10% by weight have a diameter of 10 µm and less.

In another embodiment, the particle size distribution of d(90) is in the range of from 200 µm to 400 µm, and less than 20% by weight of the total particles have a diameter of 10 µm and less, or less than 15% by weight have a diameter of 10 µm and less, or less than 10% by weight have a diameter of 10 µm and less.

The inventors have further discovered that the particle size distribution may be further advantageously influenced by forming the star-shaped crystals as described in step (iv) above.

Accordingly, performing reaction step (i) and/or crystallization step (ii) and/or re-crystallization step (iii) in combination with seeding step (iv), wherein the solvent is selected from the group of anisole, cumene; methyl ethyl ketone, methyl isobutyl ketone; and n-butyl acetate, the particle size distribution d(90) may advantageously be shifted to ranges of smaller particles as compared to a process, wherein no seeding is performed. In such process, an additional milling step is not necessary.

In one embodiment, the obtained particle size distribution d(90) is from 100 µm to 300 µm, or from 100 µm to 250 µm, if at least steps (iii) and (iv) are performed.

In one embodiment, star-shaped crystals are obtained performing at least steps (iii) and (iv), wherein anisole is used as solvent.

In one embodiment, star-shaped crystals are obtained performing at least steps (iii) and (iv), wherein methyl ethyl ketone is used as solvent.

In one embodiment, star-shaped crystals are obtained performing at least steps (iii) and (iv), wherein cumene is used as solvent.

In one embodiment, star-shaped crystals are obtained performing at least steps (iii) and (iv), wherein n-butyl acetate is used as solvent.

In one embodiment, star-shaped crystals are obtained performing at least steps (iii) and (iv), wherein methyl isobutyl ketone is used as solvent.

In one embodiment, the seeds are added at the temperature, where the mesylate dissolves in the respective solvent.

In another embodiment, the seeds are added at a temperature which is approximately 5° C. below the temperature where the mesylate dissolves in the respective solvent.

Particle size distribution ranges as determined by laser diffraction with mesylates obtained in anisole, cumene, methyl ethyl ketone, methyl isobutyl ketone and n-butyl acetate by performing at least re-crystallization step (iii) and seeding step (iv) are disclosed in the following table:

| PSD [μm] | anisole | cumene | methyl ethyl ketone | methyl isobutyl ketone | n-butyl acetate |
|---|---|---|---|---|---|
| d(90) | 184 | 152 | 210 | 137 | 136 |
| d(50) | 74 | 62 | 79 | 57 | 58 |
| d(10) | 15 | 12 | 5 | 11 | 12 |

If the process is carried out without performing seeding step (iv), the obtained particle sizes d(90) are larger, approximately by a factor of 1.5, or 2 or more, depending on the used solvent and reaction conditions. D(50) and d(10) increase accordingly.

In one embodiment, employing at least re-crystallization step (iii) in combination with seeding step (iv) and using a solvent selected from the group of anisole, cumene; methyl ethyl ketone, methyl isobutyl ketone; and n-butyl acetate; the particle size distribution of d(90) is in the range of from 100 μm to 300 μm, and less than 20% by weight of the total particles have a diameter of 10 μm and less, or less than 15% by weight have a diameter of 10 μm and less, or less than 10% by weight have a diameter of 10 μm and less.

In another embodiment, employing at least re-crystallization step (iii) in combination with seeding step (iv) and using a solvent selected from the group of anisole, cumene; methyl ethyl ketone, methyl isobutyl ketone; and n-butyl acetate; the particle size distribution of d(90) is in the range of from 100 μm to 250 μm, and less than 20% by weight of the total particles have a diameter of 10 μm and less, or less than 15% by weight have a diameter of 10 μm and less, or even less than 10% by weight have a diameter of 10 μm and less.

Step (v)

According to another aspect, in case the crystals from reaction step (i) and/or crystallization step (ii) and/or re-crystallization step (iii) and/or seeding step (iv) form agglomerates, said agglomerates may be de-agglomerated.

The term "agglomerate" encompasses crystals which adhere to each other.

Accordingly, in one embodiment, the particle size distribution of agglomerated crystals expressed in d(90) exceeds 500 μm.

Suitable methods for de-agglomeration are known in the art, e.g. by a rocking motion in a suitable device, or by milling such as a gentle milling.

The term "gentle milling" encompasses a milling which avoids the formation of particulate matter as far as possible.

Thus, in one embodiment, the process may also comprise step (v):

(v) de-agglomerating and/or milling the product formed in step (i) and/or step (ii) and/or step (iii) and/or step (iv).

Reaction Sequence for Preparing Neramexane Mesylate

One further aspect of the present invention pertains to a process, wherein 1-amino-1,3,3,5,5-pentamethylcyclohexane is obtained by a sequence of reaction steps starting from isophorone via the methods according to the reaction schemes as referred to in the Background section of the present application, e.g. the reaction sequence as disclosed by Danysz.

Accordingly, one embodiment relates to a process comprising steps (a) to (c) prior to reaction step (i):
  (a) converting isophorone to 3,3,5,5-tetramethylcyclohexanone;
  (b) converting 3,3,5,5-tetramethylcyclohexanone to 1,3,3,5,5-pentamethylcyclohexanol;
  (c) converting 1,3,3,5,5-pentamethylcyclohexanol to 1-amino-1,3,3,5,5-pentamethylcyclohexane.

Separation of By-Products

Due a possible side reaction which may occur in the above referenced sequence of producing neramexane mesylate starting form isophorone via the Grignard route, 1-amino-1,3,3-trans-5-tetramethylcyclohexane is produced as a by-product, e.g. in an amount exceeding 0.5% by weight or more. Said amine also forms a mesylate in the reaction with methane sulfonic acid. Due to similar physical properties, attempts to remove said amine being contained in 1-amino-1,3,3,5,5-pentamethylcyclohexane prior to mesylate formation by using the common purification processes such as distillation are not satisfying.

In one embodiment, crude 1-amino-1,3,3,5,5-pentamethylcyclohexane comprising 1-amino-1,3,3-trans-5-tetramethylcyclohexane is subjected to mesylate formation according to the process of the invention, wherein 1-amino-1,3,3,5,5-pentamethylcyclohexane mesylate is formed comprising 1-amino-1,3,3-trans-5-tetramethylcyclohexane mesylate.

If any one of steps (i) to (v) of the process according to the invention is performed, and the target product neramexane mesylate is isolated e.g. according to step (ii) e.g. by filtrating or centrifuging the formed crystals, the target compound is obtained in a high purity with respect to the by-product, since 1-amino-1,3,3-trans-5-tetramethylcyclohexane mesylate remains in the mother liquor, i.e. the solvent, due to its better solubility.

Therefore, in one embodiment, 1-amino-1,3,3-trans-5-tetramethylcyclohexane mesylate is separated off from 1-amino-1,3,3,5,5-pentamethylcyclohexane mesylate by employing the process according to the invention, wherein the purity of the target product is increased with respect to said by-product.

Thus, while the target compound precipitates in step (i) and/or step (ii) and/or step (iii) and/or step (iv), the by-product 1-amino-1,3,3-trans-5-tetramethylcyclohexane mesylate remains at least partially dissolved in said solvents. If the target compound neramexane mesylate is separated off e.g. by filtration or centrifugation, said by-product accumulates in the mother liquor, and thus is removed from 1-amino-1,3,3,5,5-pentamethylcyclohexane mesylate.

Another by-product which may be present in the reaction mixture formed in step (i), is 1-nitro-1,3,3,5,5-pentamethylcyclohexane. This product may be formed by oxidation of 1-amino-1,3,3,5,5-pentamethylcyclohexane, e.g. during the handling and work-up of 1-amino-1,3,3,5,5-pentamethylcyclohexane in the manufacturing sequence, or if 1-amino-1,3,3,5,5-pentamethylcyclohexane is not stored under inert gas. This compound may also be effectively removed from the target compound by employing anisole or methyl ethyl ketone, optionally in admixture with water, as solvent in the process according to the invention.

In one embodiment, the process comprises step (vi):
(vi) separating 1-amino-1,3,3-trans-5-tetramethylcyclohexane mesylate from 1-amino-1,3,3,5,5-pentamethylcyclohexane mesylate; and/or separating 1-nitro-1,3,3,5,5-pentamethylcyclohexane from 1-amino-1,3,3,5,5-pentamethylcyclohexane mesylate.

Also other substances as used or which are obtained in any one of steps (a) to (c) may be present in reaction step (i) due to a possible contamination of generated 1-amino-1,3,3,5,5-pentamethylcyclohexane. These substances are compounds which are used respectively formed in the reaction sequence according to steps (a) to (c), e.g. isophorone, 3,3,5,5-tetramethylcyclohexanone, 1-hydroxy-1,3,3,5,5-pentamethylcyclohexanol, and/or 1-N-chloroacetamido-1,3,3,5,5-pentamethylcyclohexane. Said compounds are also effectively removed from the target compound by employing anisole or methyl ethyl ketone, optionally in admixture with water.

As outlined above, anisole, methyl ethyl ketone, and methyl ethyl ketone in admixture with water allow for the preparation of 1-amino-1,3,3,5,5-pentamethylcyclohexane mesylate having a high degree of purity, a high degree of crystallinity, and a low content of particulate matter which renders the target compound to be particularly suitable for the manufacture of pharmaceutical compositions.

Preparation of
1-amino-1,3,3,5,5-pentamethylcyclohexane having a
high purity with respect to
1-amino-1,3,3-trans-5-tetramethylcyclohexane In one aspect, 1-amino-1,3,3,5,5-pentamethylcyclohexane mesylate as obtained according to separation step (vi) is converted into the free amine by subjecting the mesylate to a treatment with a base such as sodium hydroxide or potassium hydroxide.

Accordingly, the process according to the invention further comprises:
(vii) converting 1-amino-1,3,3,5,5-pentamethylcyclohexane mesylate obtained according to step (vi) to 1-amino-1,3,3,5,5-pentamethylcyclohexane.

Since the undesired by-product 1-amino-1,3,3-trans-5-tetramethylcyclohexane has already been removed according to separation step (vi), the 1-amino-1,3,3,5,5-pentamethylcyclohexane obtained according to conversion step (vii) is free from 1-amino-1,3,3-trans-5-tetramethylcyclohexane. Thus, the described sequence allows for the manufacture of 1-amino-1,3,3,5,5-pentamethylcyclohexane having an improved purity with regard to a contamination with 1-amino-1,3,3-trans-5-tetramethylcyclohexane as compared to a process wherein 1-amino-1,3,3,5,5-pentamethylcyclohexane is subjected to distillation without performing step (vi).

The term "1-amino-1,3,3,5,5-pentamethylcyclohexane free from 1-amino-1,3,3-trans-5-tetramethylcyclohexane" defines 1-amino-1,3,3,5,5-pentamethylcyclohexane which contains less than 0.05% by weight, or less than 0.01% by weight, or less than 0.005% by weight, or less than 0.001% by weight 1-amino-1,3,3-trans-5-tetramethylcyclohexane based on the total amount of 1-amino-1,3,3,5,5-pentamethylcyclohexane and 1-amino-1,3,3-trans-5-tetramethylcyclohexane as e.g. determined by gas chromatographical analysis.

Accordingly, the process according to the invention allows the formation of 1-amino-1,3,3,5,5-pentamethylcyclohexane in a high purity with respect to 1-amino-1,3,3-trans-5-tetramethylcyclohexane impurity.

Accordingly, the process according to the invention may further comprise a step (viii):
(viii) converting the 1-amino-1,3,3,5,5-pentamethylcyclohexane obtained in step (vii) into a pharmaceutically acceptable salt or derivative of 1-amino-1,3,3,5,5-pentamethylcyclohexane, said salt being different from 1-amino-1,3,3,5,5-pentamethylcyclohexane mesylate.

Further Aspects

The solvents as defined above may be used for the crystallization of neramexane mesylate. Said solvents may result in products exhibiting varying properties, e.g. varying properties with regard to yield, crystal forms, bulk density, flowability, suitability for the formulation of pharmaceutical compositions.

Crystal forms may e.g. influence the flowability of the formed mesylate or the bulk density thereof. Both properties may be of interest from a technical viewpoint. Frequently, it is requested that a product should exhibit a good flowability for the processibility into pharmaceutical compositions as well as a relatively high bulk density due to storage requirements.

According to one aspect, the present invention pertains to the use of anisole for the crystallisation and/or re-crystallization of 1-amino-1,3,3,5,5-pentamethylcyclohexane mesylate.

In another aspect, the present invention pertains to the use of cumene; methyl ethyl ketone, methyl isobutyl ketone; n-butyl acetate; optionally together with water; for the crystallisation and/or re-crystallization of 1-amino-1,3,3,5,5-pentamethylcyclo-hexane mesylate.

In one aspect, the invention relates to 1-amino-1,3,3,5,5-pentamethylcyclohexane mesylate crystals, wherein the crystals are star-shaped.

In one aspect, the invention relates to 1-amino-1,3,3,5,5-pentamethylcyclohexane mesylate crystals, wherein the crystals are star-shaped that may be obtainable by a process comprising steps (i) and/or step (iii) and (iv), and optionally step (v):
(i) reacting 1-amino-1,3,3,5,5-pentamethylcyclohexane with methane sulfonic acid in a solvent, wherein the solvent is anisole, cumene, methyl ethyl ketone, methyl isobutyl ketone or n-butyl acetate; optionally together with water; and/or
(iii) re-crystallizing the product formed in step (i) and/or step (iii) in anisole, cumene, methyl ethyl ketone, methyl isobutyl ketone or n-butyl acetate; optionally together with water;
(iv) adding 1-amino-1,3,3,5,5-pentamethylcyclohexane mesylate to step (i) and/or step (iii);
(v) de-agglomerating and/or milling the product formed in step (iii).

In one embodiment, the solvent is anisole.

In another embodiment, the solvent is selected from the group of cumene, methyl ethyl ketone, and methyl isobutyl ketone.

In another embodiment, the solvent is methyl ethyl ketone or methyl isobutyl ketone; together with water.

In another aspect, the invention relates to 1-amino-1,3,3,5,5-pentamethylcyclohexane mesylate particles, wherein less than 20% by weight of the total particles have a particle size of 10 μm and less, or wherein less than 15% by weight of the particles have a particle size of 10 μm and less, or wherein less than 10% by weight of the particles have a particle size of 10 μm and less, that may be obtainable by a process comprising at least step (i) and/or step (iii):
(i) reacting 1-amino-1,3,3,5,5-pentamethylcyclohexane with methane sulfonic acid in a solvent, wherein the solvent is anisole, cumene, methyl ethyl ketone, methyl isobutyl ketone or n-butyl acetate; optionally together with water; and/or
(iii) re-crystallizing the product formed in step (i).

In one embodiment, the solvent is anisole.

In another embodiment, the solvent is selected from the group of cumene, methyl ethyl ketone, and methyl isobutyl ketone.

In another embodiment, the solvent is methyl ethyl ketone or methyl isobutyl ketone; together with water.

In one aspect, the invention relates to a pharmaceutical composition comprising 1-amino-1,3,3,5,5-pentamethylcyclohexane mesylate crystals, wherein the crystals are star-shaped, and a pharmaceutically acceptable excipient.

In another aspect, the invention relates to a process for producing a pharmaceutical composition comprising 1-amino-1,3,3,5,5-pentamethylcyclohexane mesylate particles, wherein less than 20% by weight of the total particles have a particle size of 10 μm and less, or wherein less than 15% by weight of the particles have a particle size of 10 μm and less, or wherein less than 10% by weight of the particles have a particle size of 10 μm and less, and a pharmaceutically acceptable excipient.

In yet another aspect, the invention relates to a pharmaceutical composition comprising 1-amino-1,3,3,5,5-pentamethylcyclohexane mesylate crystals, wherein the crystals are star-shaped, and at least one pharmaceutically acceptable excipient.

In one aspect, the invention relates to a pharmaceutical composition comprising 1-amino-1,3,3,5,5-pentamethylcyclohexane mesylate particles, wherein less than 20% by weight of the total particles have a particle size of 10 μm and less, or wherein less than 15% by weight of the particles have a particle size of 10 μm and less, or wherein less than 10% by weight of the particles have a particle size of 10 μm and less; and optionally at least one pharmaceutically acceptable excipient.

In another aspect, the invention relates to a pharmaceutical composition comprising 1-amino-1,3,3,5,5-pentamethylcyclohexane which is free from 1-amino-1,3,3-trans-5-tetramethylcyclohexane, or a salt thereof, said salt being different from 1-amino-1,3,3,5,5-pentamethylcyclohexane mesylate, and optionally one or more pharmaceutically acceptable excipients.

In a further aspect, the invention relates to 1-amino-1,3,3,5,5-pentamethylcyclohexane mesylate crystals, wherein the crystals are star-shaped; or 1-amino-1,3,3,5,5-pentamethylcyclohexane mesylate particles, wherein less than 20% by weight of the total particles have a particle size of 10 μm and less, or wherein less than 15% by weight of the particles have a particle size of 10 μm and less, or wherein less than 10% by weight of the particles have a particle size of 10 μm and less; or 1-amino-1,3,3,5,5-pentamethylcyclohexane which is free from 1-amino-1,3,3-trans-5-tetramethylcyclohexane; for use as a medicament.

In a further aspect, the invention relates to 1-amino-1,3,3,5,5-pentamethylcyclohexane mesylate crystals, wherein the crystals are star-shaped; or 1-amino-1,3,3,5,5-pentamethylcyclohexane mesylate particles, wherein less than 20% by weight of the total particles have a particle size of 10 μm and less, or wherein less than 15% by weight of the particles have a particle size of 10 μm and less, or wherein less than 10% by weight of the particles have a particle size of 10 μm and less; or 1-amino-1,3,3,5,5-pentamethylcyclohexane which is free from 1-amino-1,3,3-trans-5-tetramethylcyclohexane; for use in the treatment of tinnitus.

As used herein, the term "tinnitus" includes all manifestations of subjective and objective tinnitus as well as acute, subacute and chronic forms.

In a further aspect, the invention relates to the use of 1-amino-1,3,3,5,5-pentamethylcyclohexane mesylate crystals, wherein the crystals are star-shaped; or 1-amino-1,3,3,5,5-pentamethylcyclohexane mesylate particles, wherein less than 20% by weight of the total particles have a particle size of 10 μm and less, or wherein less than 15% by weight of the particles have a particle size of 10 μm and less, or wherein less than 10% by weight of the particles have a particle size of 10 μm and less; or 1-amino-1,3,3,5,5-pentamethylcyclohexane which is free from 1-amino-1,3,3-trans-5-tetramethylcyclohexane; for the manufacture of a pharmaceutical composition for the treatment of tinnitus.

In a further aspect, the invention relates to a method of treating tinnitus in a patient in need thereof, comprising administering to the patient an effective amount of 1-amino-1,3,3,5,5-pentamethylcyclohexane mesylate crystals, wherein the crystals are star-shaped; or 1-amino-1,3,3,5,5-pentamethylcyclohexane mesylate particles, wherein less than 20% by weight of the total particles have a particle size of 10 μm and less, or wherein less than 15% by weight of the particles have a particle size of 10 μm and less, or wherein less than 10% by weight of the particles have a particle size of 10 μm and less; or 1-amino-1,3,3,5,5-pentamethylcyclohexane which is free from 1-amino-1,3,3-trans-5-tetramethylcyclohexane.

In another aspect, the invention relates to a pharmaceutically acceptable salt that may be obtained according to step (viii).

In another aspect, the invention relates to a pharmaceutically acceptable salt that may be obtained according to step (viii) for use as a medicament.

In another aspect, the invention relates to a pharmaceutically acceptable salt that may be obtained according to step (viii) for use in the treatment of tinnitus.

In another aspect, the invention relates to the use of a pharmaceutically acceptable salt that may be obtained according to step (viii) for the manufacture of a pharmaceutical composition for the treatment of tinnitus.

In another aspect, the invention relates to a method of treating tinnitus in a patient in need thereof, comprising administering to the patient an effective amount of a pharmaceutically acceptable salt that may be obtained according to step (viii).

Additional Aspects of the Invention

Additionally disclosed is a process for manufacturing 1-amino-1,3,3,5,5-pentamethylcyclohexane mesylate comprising a step (i) of reacting 1-amino-1,3,3,5,5-pentamethylcyclohexane with methane sulfonic acid in a solvent or a mixture of two or more solvents selected among acetone, anisole, butyl acetate, t-butyl methyl ether, cumene, dimethylsulphoxide, ethyl acetate, ethyl ether, ethyl formate, heptane, i-butyl acetate, i-propyl acetate, methyl acetate, methyl ethyl ketone, methyl i-butyl ketone, pentane, propyl acetate, tetrahydrofurane, 1,1-diethoxypropane, 1,1-dimethoxymethane, 2,2-dimethoxypropane, isooctane, isopropyl ether, methyl i-propyl ketone and methyltetrahydrofurane.

In one embodiment, said solvent is selected from the group of anisole, t-butyl methyl ether, cumene, dimethylsulphoxide, heptane, methyl ethyl ketone, methyl i-butyl ketone, pentane, tetrahydrofuran, and mixtures thereof.

In another embodiment, said solvent is anisole or a mixture of anisole and at least one of the other solvents as defined above.

In another embodiment, the ratio of the volume of solvent to weight of 1-amino-1,3,3,5,5-pentamethylcyclohexane is from 5:1 to 50:1 (ml/g).

In another embodiment, the temperature within step (i) is from −20° C. to 120° C.

In another embodiment, said process comprises steps (a) to (c) prior to step (i):
  (a) converting isophorone to 3,3,5,5-tetramethylcyclohexanone;
  (b) converting 3,3,5,5-tetramethylcyclohexanone to 1,3,3,5,5-pentamethylcyclohexanol;
  (c) converting 1,3,3,5,5-pentamethylcyclohexanol to 1-amino-1,3,3,5,5-pentamethylcyclohexane.

In yet another embodiment, 1-amino-1,3,3,5,5-pentamethylcyclohexane mesylate is isolated from the reaction mixture produced in step (i) by a step (ii) of crystallization.

In another embodiment, crystallization is achieved by reducing the temperature of the reaction mixture of step (i), adding anti-solvents or distilling off partially the solvent used in step (i).

In another embodiment, the temperature of the mixture of step (i) is reduced to a temperature within the range of −20° C. to 50° C.

In yet another embodiment, the invention relates to the use of anisole or a mixture of anisole and at least one of the other solvents as defined above for the crystallisation of 1-amino-1,3,3,5,5-pentamethylcyclohexane mesylate.

The process according to the invention allows for obtaining Neramexane mesylate in high yields and having a particle size distribution that is directly suitable for tabletting, i.e. without milling prior to the tabletting. This is particularly advantageous for an economical industrial process.

Furthermore, Neramexane mesylate is obtained in a high purity, in particular with respect to impurities comprising alkyl mesylates. Such impurities should be as low as reasonably practicable due to their suspected toxic effects.

In one embodiment, the invention relates to a 1-amino-1,3,3,5,5-pentamethylcyclohexane mesylate containing 100 ppm or less methane sulfonic acid alkyl ester.

Also disclosed is a process for manufacturing 1-amino-1,3,3,5,5-pentamethylcyclohexane mesylate comprising a step (i) of reacting 1-amino-1,3,3,5,5-pentamethylcyclohexane with methane sulfonic acid in a solvent or a mixture of two or more solvents selected among acetone, anisole, butyl acetate, t-butyl methyl ether, cumene, dimethylsulphoxide, ethyl acetate, ethyl ether, ethyl formate, heptane, i-butyl acetate, i-propyl acetate, methyl acetate, methyl ethyl ketone, methyl i-butyl ketone, pentane, propyl acetate, tetrahydrofurane, 1,1-diethoxypropane, 1,1-dimethoxymethane, 2,2-dimethoxypropane, isooctane, isopropyl ether, methyl-1-propyl ketone and methyltetrahydrofurane. Some of the solvents listed above are classified as "Class 3 solvents" according to the ICH guidelines "Guidance for Industry" issued by the US Department of Health and Human Services et al, November 2003 Revision 1 "Q3C—Tables and List".

In one embodiment, said solvent is selected from at least one of acetone, anisole, t-butyl methyl ether, cumene, dimethylsulphoxide, heptane, methyl ethyl ketone, methyl ethyl ketone in admixture with water, e.g. in an amount of water of 0.01 to 5% by weight, methyl i-butyl ketone, pentane, tetrahydrofurane and mixtures thereof.

In one further embodiment, said solvent is anisole or a mixture of anisole and at least one of acetone, butyl acetate, t-butyl methyl ether, cumene, dimethylsulphoxide, ethyl acetate, ethyl ether, ethyl formate, heptane, i-butyl acetate, i-propyl acetate, methyl acetate, methyl ethyl ketone, methyl i-butyl ketone, pentane, propyl acetate, tetrahydrofurane, 1,1-diethoxypropane, 1,1-dimethoxymethane, 2,2-dimethoxypropane, isooctane, isopropyl ether, methyl i-propyl ketone and methyltetrahydrofurane.

In one embodiment, said mixture is a mixture of anisole and heptane.

In one further embodiment, the solvent is methyl ethyl ketone in admixture with an amount of water of 0.01 to 5% by weight, wherein the reaction according to step (i) is carried out optionally in the presence of neramexane mesylate seeds. These seeds may be added prior to, together with, or after the addition of methane sulfonic acid to the mixture of neramexane and solvent.

In another embodiment, the amount of water is from 0.1 to 5% by weight, or from 0.1 to 3% by weight or from 0.5 to 3% by weight, or from 0.5 to 2.5% by weight, or from 1 to 2% by weight.

One aspect of the present invention pertains to a process as outlined above wherein in said step (i) the ratio of the volume of solvent to weight of 1-amino-1,3,3,5,5-pentamethylcyclohexane is from 5:1 to 50:1 (ml/g).

In one embodiment, the ratio of the volume of solvent to weight of 1-amino-1,3,3,5,5-pentamethylcyclohexane is from 5:1 to 20:1 (ml/g).

In another embodiment, the ratio of the volume of solvent to weight of 1-amino-1,3,3,5,5-pentamethylcyclohexane is from 5:1 to 10:1 (ml/g).

In another embodiment, the ratio of the volume of solvent to weight of 1-amino-1,3,3,5,5-pentamethylcyclohexane is from 5:1 to 8:1 (ml/g).

One other aspect of the present invention pertains to process, wherein the temperature within step (i) is from −20° C. to 120° C.

In one embodiment of the present invention the temperature within step (i) is between 50° C. and 80° C., from 70° C. to 80° C., or is 80° C.

One further aspect of the present invention pertains to process, wherein 1-amino-1,3,3,5,5-pentamethylcyclohexane is obtained by a sequence of reaction steps starting from isophorone via the methods according to the reaction schemes shown in the Background section of the present application.

Accordingly, one embodiment relates to a process comprising steps (a) to (c) prior to step (i):
(a) converting isophorone to 3,3,5,5-tetramethylcyclohexanone;
(b) converting 3,3,5,5-tetramethylcyclohexanone to 1,3,3,5,5-pentamethylcyclohexanol;
(c) converting 1,3,3,5,5-pentamethylcyclohexanol to 1-amino-1,3,3,5,5-pentamethylcyclohexane.

One embodiment of the instant invention refers to a process, wherein the 1-amino-1,3,3,5,5-pentamethylcyclohexane mesylate is isolated from the reaction mixture of step (i) by a step (ii) of crystallization.

Crystallization may be achieved by reducing the temperature of the reaction mixture of step (i), adding of anti-solvents or distilling off partially the solvent used in step (i), or a combination of two or more of these measures.

The term "anti-solvent" encompasses any solvent that, when added to the addition salt formed in step (i), results in the precipitation or the crystallization of the mesylate.

In order to achieve crystallization in one embodiment, temperature may be reduced to an end temperature within the range of −20° C. to 50° C. In one embodiment the end temperature of crystallization is between 5° C. to 15° C. In one further embodiment the end temperature of crystallization is 20° C. In another embodiment the end temperature of crystallization is 10° C.

In one embodiment of the present invention, the time of stirring at the end temperature of crystallization is 3 hours or less, e.g. from 10 minutes to 2 hours.

In one embodiment of the instant invention, the methane sulfonic acid is added into the solvent of step (i).

One embodiment, the instant invention pertains to 1-amino-1,3,3,5,5-pentamethylcyclohexane mesylate in the form of crystals having a particle size distribution of d(90) in the range of from 100 µm to 500 µm, or 100 µm to 300 µm, or 150 µm to 300 µm, or 200 µm to 275 µm, or 200 µm to 250 µm as measured with laser diffraction.

In a further embodiment, the 1-amino-1,3,3,5,5-pentamethylcyclohexane mesylate in the form of crystals having a particle size distribution of d(90) in the range of 200 µm to 300 µm and 10% or less having a particle size of 55 µm or less, e.g. 5 µm or less.

The particle size range of the resulting crystals is sufficient that further milling of the crystals prior to pressing them to a tablet is not necessary. It is, however, well within the ambit of the present invention to mill or sieve the particles as obtained from the process as claimed herein.

In one embodiment of the present invention, anisole is used as the solvent and the crystallization is carried out in such a manner that the neramexane mesylate is obtained in particle sizes that allow direct tabletting, i.e. are obtained such that milling or sieving is not necessary.

In this respect, it is noteworthy that crystals having particle sizes of more than 500 µm can often only be directly pressed to a pharmaceutical composition such as a tablet form under difficulties, since they are relatively coarse and hard and render the tablet inhomogeneous. Prior to the pressing, such coarse and hard crystals may have to be broken by appropriate means known in the art.

In one embodiment, the present invention pertains to the use of anisole for the crystallization of 1-amino-1,3,3,5,5-pentamethylcyclohexane mesylate In one embodiment, 1-amino-1,3,3,5,5-pentamethylcyclohexane mesylate may be also obtained by using a mixture of anisole and heptane.

In one embodiment, the present invention pertains to 1-amino-1,3,3,5,5-pentamethylcyclohexane mesylate, as produced according to the process claimed herein, which contains 1% by weight or less residual solvent.

In one embodiment, the 1-amino-1,3,3,5,5-pentamethylcyclohexane mesylate contains 0.50% by weight or less residual solvent. In a further embodiment the 1-amino-1,3,3,5,5-pentamethylcyclohexane mesylate contains 0.05% by weight or less residual solvent.

In one embodiment of the process according to the invention, 1-amino-1,3,3,5,5-pentamethylcyclohexane is dissolved or dispersed or suspended in a solvent or a mixture of two or more of said solvents as defined above. Subsequent to the dissolving or dispersing or suspending, methane sulfonic acid is added in order to allow for the formation of the mesylate.

In one embodiment, methane sulfonic acid is added in the form of a solution of said acid in said solvent or a mixture of two or more of said solvents, wherein the solvent or the mixture of two or more of said solvents for said 1-amino-1,3,3,5,5-pentamethylcyclohexane and the solvent or the mixture of two or more of said solvents for said methane sulfonic acid may be independently selected from each other.

In one embodiment, the solvent for 1-amino-1,3,3,5,5-pentamethylcyclohexane and the solvent for methane sulfonic acid is or comprises anisole.

The precipitated and/or crystallized mesylate may be separated off from the reaction mixture by filtration.

FIGURES

FIG. 1 presents the isolated star-shaped crystals, when 1% (weight/weight), 2.5%, 5% and 7.5% of 1-amino-1,3,3,5,5-pentamethylcyclohexane mesylate seeds are added in seeding step (iv) of the process according to the invention subsequent to reaction step (i) or re-crystallization step (iii), wherein the solvent is anisole (see Example 3).

Figure 2:
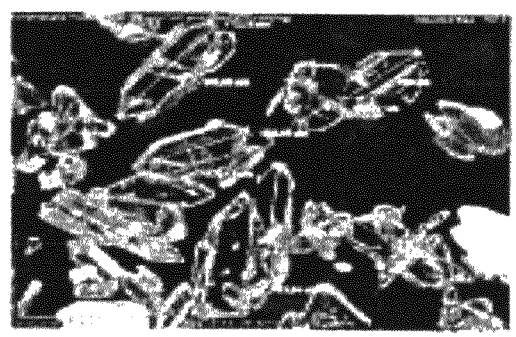

FIG. 2 presents columnar crystals if no 1-amino-1,3,3,5,5-pentamethylcyclohexane mesylate seeds are added in the process according to the invention in reaction step (i) and/or re-crystallization step (iii), wherein the solvent is anisole (see Example 1).

Figure 3:
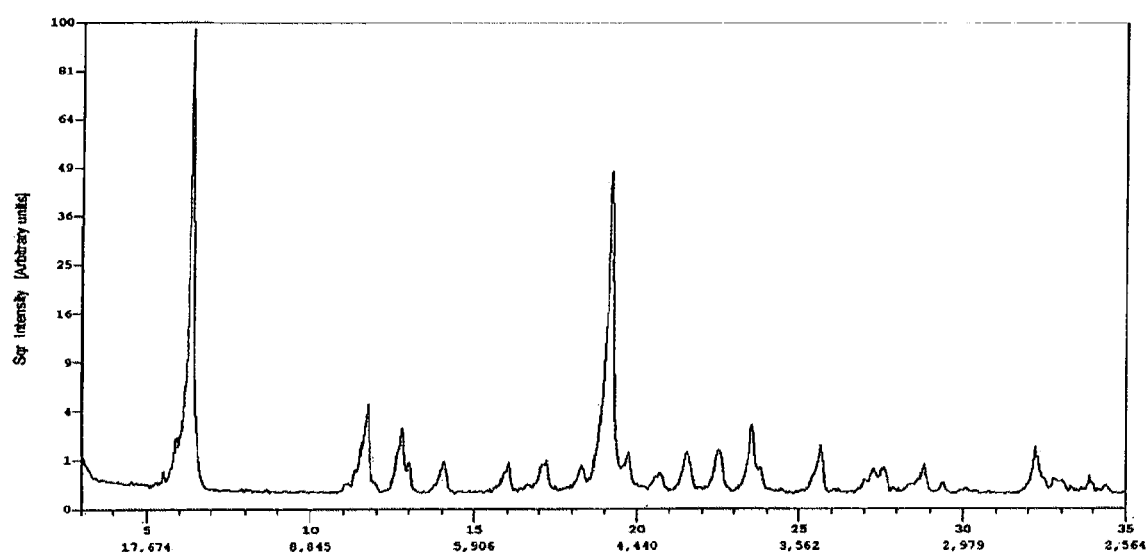

FIG. 3 presents a XRD analysis of neramexane mesylate obtained according to Example 6. The x-axis shows 2Θ [deg]/d [Å], the y-axis the intensity in arbitrary units (transmission diffractometer, U=40 kV, I=35 mA, Cu, λ=1.54186 Å).

Figure 4:
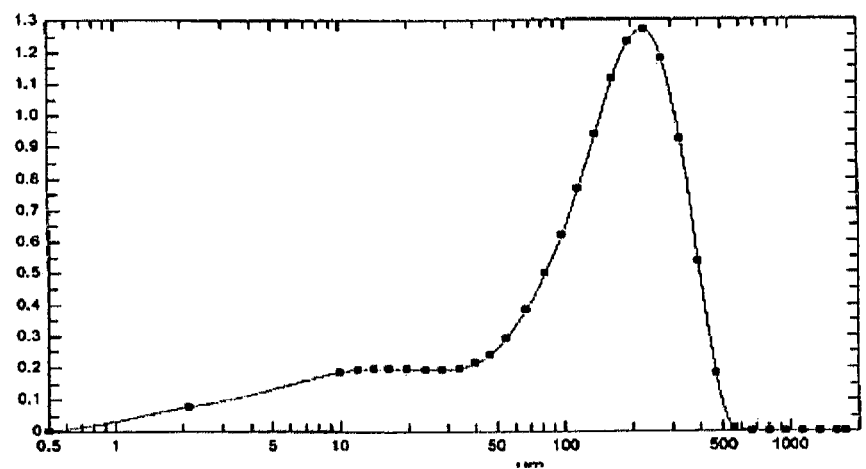

FIG. 4 presents the particle size distribution of neramexane mesylate obtained according to Example 6. The x-axis represents the particle size in µm, the y-axis the density allocation. The determination was performed using a HELOS laser diffraction sensor (Sympatec GmbH).

Figure 5:
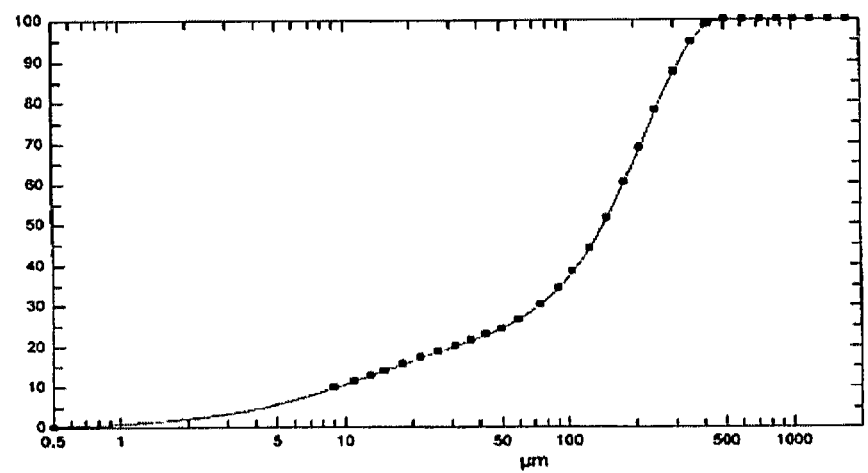

FIG. 5 presents the corresponding modal distribution size. The x-axis represents the particle size in µm, the y-axis the sum distribution in %.

Figure 6:
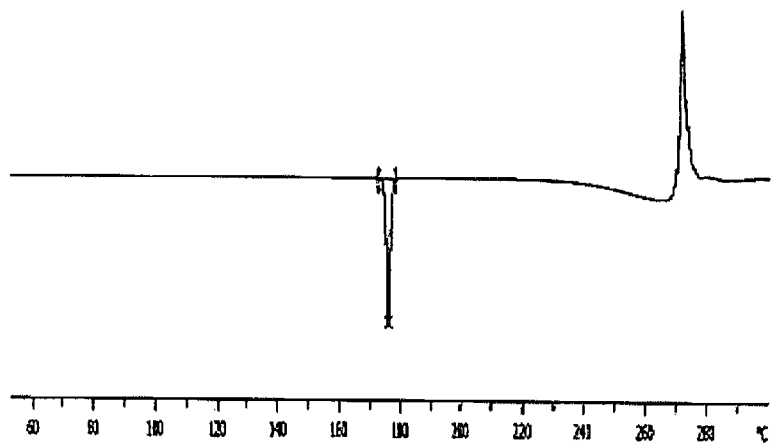

FIG. 6 presents a differential scanning calorimetry (DSC) diagram of neramexane mesylate obtained according to Example 6. The heating rate is 5° C./min.

The invention is now described with reference to the following examples. These examples are provided for the purpose of illustration only and the invention should not be construed as being limited to these examples, but rather should be construed to encompass any and all variations which become evident as a result of the teaching provided herein. The following materials and methods are provided with respect to the subsequent examples but do not limit a multiplicity of materials and methodologies encompassed by the present invention.

EXAMPLES

Example 1

Use of Anisole as Solvent in Reaction Step (i)

To a jacketed three-neck 250 ml laboratory glass reactor equipped with overhead stirrer, thermometer and bottom discharge valve 15.0 g (1 eq, 88.59 mmol) 1-amino-1,3,3,5,5-pentamethyl-cyclohexane and 75.0 ml anisole is added. The mixture is heated to 80° C. To the mixture (between 80-85° C., during 30-40 minutes) 5.76 ml (1.0 eq, 88.59 mmol) methane sulfonic acid in 22.5 ml anisole is added. After addition of methane sulfonic acid, the reaction mixture is stirred at 50° C. for one hour. The reaction mixture is cooled to 10° C. during 4 hours using a programmable Huber thermostat. The mixture is stirred for a further 2 hours at 10° C. The precipitated and crystallized product is filtered off and washed twice with anisole. The product (1-amino-1,3,3,5,5-pentamethylcyclohexane mesylate) is dried at 60° C. to constant weight overnight. The melting point of mesylate salt is 175° C. (capillary method). The yield of product is 91%.

Example 2

Particle Size Distribution of Neramexane Mesylate Obtained in Example 1

The crystals obtained in the process of Example 1 are analysed regarding the crystal size and size distribution. A commercial Malvern Mastersizer 2000 is employed. The samples are dispersed in rapeseed oil. The results are as follows:

| Particle size Distribution | Size in µm |
|---|---|
| d(90) | 264.5 |
| d(50) | 129.4 |
| d(10) | 52.3 |

The total amount of particles having a particle size of 10 μm and less is less than 1% by weight. The particle size distribution and the particles sizes are appropriate to use the product directly without milling to form tablets according to conventional methods.

Example 3

Use of Anisole as Solvent in Reaction Step (i) and Seeding Step (iv)

To a jacketed three-neck 250 ml laboratory glass reactor equipped with overhead stirrer, thermometer and bottom discharge valve 15.0 g (1 eq, 88.59 mmol) 1-amino-1,3,3,5,5-pentamethylcyclohexane and 75.0 ml anisole is added. The mixture is heated to 80° C. To the mixture (between 80-85° C., during 30-40 minutes) 5.76 ml (1.0 eq, 88.59 mmol) methane sulfonic acid in 22.5 ml anisole is added. After addition of methane sulfonic acid, 1-amino-1,3,3,5,5-pentamethylcyclohexane mesylate is added. The reaction mixture is cooled to 20° C. during 4 hours using a programmable Huber thermostat. The mixture is stirred for a further 2 hours at 20° C. The precipitated and crystallized product is filtered off and washed twice with anisole. The product 1-amino-1,3,3,5,5-pentamethylcyclohexane mesylate is dried at 60° C. to constant weight overnight.

FIG. 1 shows the isolated star-shaped crystals, when 1% (weight/weight), 2.5%, 5% and 7.5% of 1-amino-1,3,3,5,5-pentamethylcyclohexane mesylate seeds are added.

The particle size distribution is as follows (5% by weight seeds added):

| Particle size Distribution | Size in μm |
|---|---|
| d(90) | 184 |
| d(50) | 74 |
| d(10) | 15 |

The particle size distribution and the particles sizes are appropriate to use the product directly without milling to form tablets according to conventional methods.

Example 4

Use of Methyl Ethyl Ketone as Solvent in Reaction Step (i) and Crystallization Step (ii)

To a 50 l steel reactor equipped with overhead stirrer, thermometer and bottom discharge valve 3.33 kg 1-amino-1,3,3,5,5-pentamethylcyclohexane and 30.0 l methyl ethyl ketone is added. The mixture is heated to 50 to 55° C. To the mixture 1.99 kg methane sulfonic acid is added within 60 min, keeping the temperature at 50° C. to 55° C. After addition of methane sulfonic acid, the reaction mixture is stirred at 50° C. to 55° C. for one hour. The reaction mixture is cooled to 20 to 25° C. within 3 hours. The mixture is stirred for another hour at 20 to 25° C. The precipitated and crystallized product is filtered off and washed twice with methyl ethyl ketone. The isolated 1-amino-1,3,3,5,5-pentamethylcyclohexane mesylate is dried at 50° C. to constant weight in vacuum at 50° C. to yield 5 kg of colorless crystals.

Example 5

Use of Methyl Ethyl Ketone as Solvent in Reaction Step (i) and Re-Crystallization Step (iii)

To a jacketed three-neck 1000 ml laboratory glass reactor equipped with overhead stirrer, thermometer and bottom discharge valve 15.0 g (1 eq, 88.59 mmol) 1-amino-1,3,3,5,5-pentamethyl-cyclohexane and 330 ml methyl ethyl ketone is added. The mixture is heated to 80° C. To the mixture (between 80-85° C., during 30-40 minutes) 5.76 ml (1.0 eq, 88.59 mmol) methane sulfonic acid is added. After addition of methane sulfonic acid, the reaction mixture is stirred at 80° C. for one hour. The reaction mixture is cooled to 10° C. during 4 hours using a programmable Huber thermostat, wherein neramexane mesylate starts precipitating in crystallized form. The mixture is stirred for a further 2 hours at 10° C. The precipitated and crystallized product is filtered off and washed twice with methyl ethyl ketone. The obtained 1-amino-1,3,3,5,5-pentamethylcyclohexane mesylate is dried at 60° C. to constant weight overnight. The melting point is 175° C. (capillary method). The yield of product is 95%.

Example 6

Use of Anisole in Reaction Step (i), Crystallization Step (ii) and Re-Crystallization Step (iii)

Reaction According to Step (i) and Crystallization According to Step (ii)

To a 2.500 l reactor equipped with stirrer, temperature control and bottom discharge valve, 762 kg anisole and 110 kg distilled 1-amino-1,3,3,5,5-pentamethylcyclohexane are added. The mixture is stirred for 30 min at a temperature of from 20 to 30° C. Subsequently to the stirring, the mixture is discharged from the reactor and filtered through a cartridge filter having a mesh size of 0.65 μm. The filtered solution is diluted with 218 kg anisole and is re-filtered through a cartridge filter having a mesh size of 0.65 μm. The reactor is re-charged with the filtered mixture. The mixture is stirred at 45 to 55 rpm and is heated to a temperature of from 80 to 82° C. A stirred mixture of 62.5 kg methane sulfonic acid and 54 kg anisole is added to the stirred and heated mixture of neramexane in anisole during 60 to 70 min, wherein the mixture of acid and anisole are filtered through a cartridge filter having a mesh size of 0.65 μm. After the charging of the acid, the filter is washed with another 54 kg anisole. The mixture in the reactor is stirred at a temperature between 80 and 82° C. at 45 to 55 rpm for 50 to 70 min. Subsequently, the mixture is cooled to a temperature between 28° C. and 32° C. during 2.5 to 3.5 h. The mixture is stirred for another 2 h. Subsequent to the stirring, the mixture is centrifuged in three portions. Each of the centrifuged portions is washed three times with 50 kg anisole, respectively.

Re-Crystallization According to Step (iii)

The reactor is re-charged with 170 kg of the mesylate obtained by the above centrifugation and with 1683 kg anisole. The mixture is heated to a temperature of from 88 to 90° C. employing a stirring rate of from 70 to 75 rpm. After reaching the temperature, the mixture is stirred for another 60 min. Subsequently, the mixture is cooled down to a temperature between 28° C. and 32° C. during 1.5 h to 2 h employing a stirring rate of from 70 to 75 rpm. The mixture is stirred at 28° C. to 32° C. for another 2 h employing a stirring rate of from 70 to 75 rpm. The product is centrifuged as described above.

Subsequent to the first re-crystallization step, 160 kg re-crystallized product in 1584 kg anisole is subjected to a second re-crystallization step in a similar manner as described for the first re-crystallization step. The mixture is heated to a temperature of from 88° C. to 90° C. employing a stirring rate of from 70 to 75 rpm. After reaching the temperature, the mixture is stirred for another 60 min. Subsequently, the mixture is cooled down to a temperature between 28° C. and 32° C. during 1.5 h to 2 h employing a stirring rate of from 70 to 75 rpm. The mixture is stirred at 28° C. to 32° C. for 2 h employing a stirring rate of from 70 to 75 rpm. The product is centrifuged and washed as described above.

The product is dried at 55 to 65° C. at about 10 mbar vacuum. The white lath-like crystals have a melting point of 175.08° C. (DSC method; FIG. 6).

The product is converted to the free base, and a purity test is performed by gas chromatographical analysis:

| | |
|---|---|
| 1-amino-1,3,3,5,5-pentamethylcyclohexane | >98.5% |
| 1-hydroxy-1,3,3,5,5-pentamethlycyclohexane | ≤0.10% |
| 1-N-chloroacetamido-1,3,3,5,5-pentamethlycyclohexane | ≤0.10% |
| 1-nitro-1,3,3,5,5-pentamethylcyclohexane | ≤100 ppm |
| 1-amino-1,3,3-trans-5-tetramethylcyclohexane | not detected |

Example 7

Use of a Mixture of Methyl Ethyl Ketone/Water in Reaction Step (i) and Crystallization Step (ii)

A reactor is charged with 168 kg 1-amino-1,3,3,5,5-pentamethylcyclohexane, 1680 kg methyl ethyl ketone and 6 l water. 1.5 kg 1-amino-1,3,3,5,5-pentamethylcyclohexane mesylate is added to the stirred mixture. Subsequently, 101 kg methane sulfonic acid are added to the stirred mixture. As soon as the acid is added, 1.5 kg 1-amino-1,3,3,5,5-pentamethylcyclohexane mesylate starts crystallizing. The precipitating and precipitated product is continuously removed during the addition of the acid and is wet-milled. The milled product is re-charged into the reactor. After the precipitation is completed, the product is centrifuged and washed with methyl ethyl ketone. The product is dried at 60° C. in vacuum. 248 kg product are obtained in the form of white to colourless crystals. The crystals are columnar. The product melts between 173 and 175° C. (capillary method).

Example 8

Re-Crystallization of Neramexane Mesylate According to Step (iii) Using Cumene as Solvent 20 ml cumene are necessary to dissolve 1 g neramexane mesylate at 104° C. The mixture is cooled down to ambient temperature. The re-crystallized product is isolated via centrifugation. The obtained crystals are columnar.

Example 9

Re-Crystallization of Neramexane Mesylate According to Step (iii) and Seeding According to Step (iv) Using Cumene as Solvent 1 g neramexane mesylate is dissolved in 20 ml cumene at 104° C. The mixture is cooled down to 90° C., where 5% by weight neramexane mesylate is added. Subsequently, the mixture is cooled down to ambient temperature. The re-crystallized product is isolated via centrifugation in a yield of 95%. The obtained crystals are star-shaped.

Example 10

Re-Crystallization of Neramexane Mesylate According to Step (iii) Using Methyl Ethyl Ketone as Solvent 22 ml methyl ethyl ketone are necessary to dissolve 1 g neramexane mesylate at 80° C. The mixture is cooled down to ambient temperature. The re-crystallized product is isolated via centrifugation. The obtained crystals have the form of plates in admixture with columnar crystals.

Example 11

Re-Crystallization of Neramexane Mesylate According to Step (iii) and Seeding According to Step (iv) Using Methyl Ethyl Ketone as Solvent 1 g neramexane mesylate is dissolved in 22 ml methyl ethyl ketone at 80° C. The mixture is cooled down to 79° C., where 5% by weight neramexane mesylate is added. Subsequently, the mixture is cooled down to ambient temperature. The re-crystallized product is isolated via centrifugation in a yield of 95%. The obtained crystals are star-shaped.

Example 12

Re-Crystallization of Neramexane Mesylate According to Step (iii) Using Methyl Isobutyl Ketone as Solvent 20 ml methyl isobutyl ketone are necessary to dissolve 1 g neramexane mesylate at 100° C. The mixture is cooled down to ambient temperature. The re-crystallized product is isolated via centrifugation. The obtained crystals are columnar.

Example 13

Re-Crystallization of Neramexane Mesylate According to Step (iii) and Seeding According to Step (iv) Using Methyl Isobutyl Ketone as Solvent 1 g neramexane mesylate is dissolved in 20 ml methyl isobutyl ketone at 100° C. The mixture is cooled down to 95° C., where 5% by weight neramexane mesylate is added. Subsequently, the mixture is cooled down to ambient temperature. The re-crystallized product is isolated via centrifugation in a yield of 95%. The obtained crystals are star-shaped.

Example 14

Re-Crystallization of Neramexane Mesylate According to Step (iii) Using N-Butyl Acetate as Solvent 23 ml n-butyl acetate are necessary to dissolve 1 g neramexane mesylate at 100° C. The mixture is cooled down to ambient temperature. The re-crystallized product is isolated via centrifugation. The obtained crystals are columnar.

Example 15

Re-Crystallization of Neramexane Mesylate According to Step (iii) and Seeding According to Step (iv) Using N-Butyl Acetate as Solvent 1 g neramexane mesylate is dissolved in 23 ml n-butyl acetate at 100° C. The mixture is cooled down to 95° C., where 5% by weight neramexane mesylate is added. Subsequently, the mixture is cooled down to ambient temperature.

The re-crystallized product is isolated via centrifugation in a yield of 96%. The obtained crystals are star-shaped.

Example 16

Re-Crystallization of Neramexane Mesylate According to Step (iii) Using Anisole as Solvent 10 ml anisole are necessary to dissolve 1 g neramexane mesylate at 87° C. The mixture is cooled down to ambient temperature. The re-crystallized product is isolated via centrifugation. The obtained crystals are columnar.

Example 17

Re-Crystallization of Neramexane Mesylate According to Step (iii) and Seeding According to Step (iv) Using Anisole as Solvent 1 g neramexane mesylate is dissolved in 10 ml anisole at 90° C. The mixture is cooled down to 85° C., where milled neramexane mesylate is added. Subsequently, the mixture is cooled down to ambient temperature. The re-crystallized product is isolated via vacuum filtration and dried under vacuum at 60° C. until constant weight (Yield about 95%). The obtained crystals are star-shaped.

The following table shows the particle size distribution in dependence from the amount of seeds:

|  | 1% seeds | 2.5% seeds | 5% seeds | 7.5% seeds |
| --- | --- | --- | --- | --- |
| d(10) [µm] | 69 | 36 | 24 | 21 |
| d(50) [µm] | 181 | 119 | 86 | 76 |
| d(90) [µm] | 377 | 330 | 215 | 243 |

The amount of particulate matter is below 5% by weight, respectively.

Example 18

Re-Crystallization of Neramexane Mesylate According to Step (iii) and Seeding According to Step (iv) Using Tetrahydrofurane as Solvent 20 ml tetrahydrofurane are necessary to dissolve 1 g neramexane mesylate at 60° C. The mixture is cooled down to 57° C., where 5% by weight neramexane mesylate is added. Subsequently, the mixture is cooled down to ambient temperature. The re-crystallized product is isolated via centrifugation in a yield of 89%. The obtained crystals have the form of plates.

Example 19

Comparison

Re-Crystallization of Neramexane Mesylate According to Step (iii) Using Toluene as Solvent 20 ml toluene are necessary to dissolve 1 g neramexane mesylate at 80° C. The mixture is cooled down to ambient temperature. The re-crystallized product is isolated via centrifugation.

Example 20

Re-Crystallization of Neramexane Mesylate According to Step (iii) and Seeding According to Step (iv) Using Toluene as Solvent 1 g neramexane mesylate is dissolved in 20 ml toluene at 80° C. The mixture is cooled down to 79° C., where 5% by weight neramexane mesylate is added. Subsequently, the mixture is cooled down to ambient temperature. The re-crystallized product is isolated via centrifugation. The obtained crystals are star-shaped.

Example 21

Comparison

Re-Crystallization of Neramexane Mesylate According to Step (iii) Using a Mixture of Acetone/Water (99/1 (Volume/Volume) as Solvent 100 ml of the mixture of acetone and water are necessary to dissolve 1 g neramexane mesylate at 40° C. The mixture is cooled down to ambient temperature. The re-crystallized product is isolated via centrifugation in a yield of 66%.

Example 22

Comparison

Re-Crystallization of Neramexane Mesylate According to Step (iii) Using Dichloromethane as Solvent 55 ml of dichloromethane are necessary to dissolve 1 g neramexane mesylate at 40° C. The mixture is cooled down to ambient temperature. The re-crystallized product is isolated via centrifugation in a yield of 87%.

The invention claimed is:

1. A process for manufacturing 1-amino-1,3,3,5,5-pentamethylcyclohexane mesylate comprising step (i):
   (i) reacting 1-amino-1,3,3,5,5-pentamethylcyclohexane with methane sulfonic acid in a solvent of anisole or methyl ethyl ketone or a solvent mixture of anisole or methyl ethyl ketone with one or more solvents selected from the group consisting of cumene, pentane, hexane, heptane, isooctane, methyl acetate, propyl acetate, isopropyl acetate, n-butyl acetate, isobutyl acetate, methyl isopropylketone, methyl isobutyl ketone, dimethyl sulphoxide, tetrahydrofuran, methyltetrahydrofuran, 1,1-diethoxypropane, 1,1-dimethoxymethane, and 2,2-dimethoxypropane; wherein the reaction results in the formation of a product of 1-amino-1,3,3,5,5-pentamethylcyclohexane mesylate.

2. The process according to claim 1, wherein the solvent is anisole, or the solvent mixture is anisole with one or more solvents selected from the group consisting of cumene, pentane, hexane, heptane, isooctane, methyl acetate, propyl acetate, isopropyl acetate, n-butyl acetate, isobutyl acetate, methyl isopropyl ketone, methyl isobutyl ketone, dimethyl sulphoxide, tetrahydrofuran, methyltetrahydrofuran, 1,1-diethoxypropane, 1,1-dimethoxymethane, and 2,2-dimethoxypropane; and optionally methyl ethyl ketone.

3. The process according to claim 1, wherein the solvent further includes water dissolved therein.

4. The process according to claim 3, wherein the solvent is methyl ethyl ketone and water or the solvent mixture is methyl ethyl ketone, water and one or more solvents selected from the group consisting of tetrahydrofuran, 1,1-diethoxypropane, 1,1-dimethoxymethane, 2,2-dimethoxypropane, methyl isopropyl ketone, and methyl isobutyl ketone.

5. The process according to claim 3, wherein the solvent includes from 0.1 to 10% by weight water based on the total amount of water and solvent.

6. The process according to claim 1, wherein in step (i) the ratio of the volume of solvent to the weight of 1-amino-1,3,3,5,5-pentamethylcyclohexane is from 5:1 to 50:1 (ml/g).

7. The process according to claim 1, wherein the temperature within step (i) is from −20° C. to 120° C.

8. The process according to claim 1, wherein the temperature within step (i) is from 0° C. to 60° C.

9. The process according to claim 8, wherein the solvent is anisole or methyl ethyl ketone in a solvent mixture with one or more solvents selected from the group consisting of cumene, pentane, hexane, heptane, isooctane, methyl isopropyl ketone, methyl isobutyl ketone, tetrahydrofuran, and mixtures thereof, and wherein the solvent optionally further includes water dissolved therein.

10. The process according to claim 1, further comprising step (ii):
(ii) isolating 1-amino-1,3,3,5,5-pentamethylcyclohexane-mesylate crystalline product from the reaction mixture of step (i) by crystallization.

11. The process according to claim 10, wherein the crystallization in step (ii) is achieved by reducing the temperature of the reaction mixture of step (i), adding anti-solvents, or distilling off partially the solvent used in step (i).

12. The process according to claim 10, wherein in step (ii) the temperature is reduced to a temperature within the range of −20° C. to 50° C.

13. The process according to claim 1, further comprising at least one of the steps (iii) to (v) subsequent to step (i):
(iii) re-crystallizing the product formed in step (i) from a mixture of one or more solvents selected from the group consisting of anisole, cumene, pentane, hexane, heptane, isooctane, methyl acetate, propyl acetate, isopropyl acetate, n-butyl acetate, isobutyl acetate, methyl ethyl ketone, methyl isopropyl ketone, methyl isobutyl ketone, dimethyl sulphoxide, tetrahydrofuran, methyltetrahydrofuran, 1,1-diethoxypropane, 1,1-dimethoxymethane, and 2,2-dimethoxypropane;
(iv) adding 1-amino-1,3,3,5,5-pentamethylcyclohexane mesylate in any one of the preceding steps (i) or (iii);
(v) de-agglomerating and/or milling the product formed in any one of the preceding steps (i), (iii), or (iv).

14. The process according to claim 10, further comprising at least one of the steps (iii) to (v) subsequent to steps (i) or (ii):
(iii) re-crystallizing the product formed in step (i) or step (ii) from a mixture of one or more solvents selected from the group consisting of anisole, cumene, pentane, hexane, heptane, isooctane, methyl acetate, propyl acetate, isopropyl acetate, n-butyl acetate, isobutyl acetate, methyl ethyl ketone, methyl isopropyl ketone, methyl isobutyl ketone, dimethyl sulphoxide, tetrahydrofuran, methyltetrahydrofuran, 1,1-diethoxypropane, 1,1-dimethoxymethane, and 2,2-dimethoxypropane;
(iv) adding 1-amino-1,3,3,5,5-pentamethylcyclohexane mesylate in any one of the preceding steps (i) to (iii);
(v) de-agglomerating and/or milling the product formed in any one of the preceding steps (i) to (iv).

15. The process according to claim 13, wherein in step (i) and/or step (iii) said solvent is anisole or methyl ethyl ketone or the solvent mixture is anisole or methyl ethyl ketone and one or more solvents selected from the group consisting of cumene, methyl isopropyl ketone, methyl isobutyl ketone, tetrahydrofuran, n-butyl acetate, and mixtures thereof; and optionally further includes water, and wherein in step (i) and/or step (iii) the temperature is from 60° C. to 120° C.

16. The process according to claim 14, wherein in step (i) and/or step (iii) said solvent is anisole or methyl ethyl ketone or the solvent mixture is anisole or methyl ethyl ketone and one or more solvents selected from the group consisting of cumene, methyl isopropyl ketone, methyl isobutyl ketone, tetrahydrofuran, n-butyl acetate, and mixtures thereof; and optionally further includes water, and wherein in step (i) and/or step (iii) the temperature is from 60° C. to 120° C.

17. The process according to claim 1, further comprising steps (a) to (c) prior to step (i):
(a) converting isophorone to 3,3,5,5-tetramethylcyclohexanone;
(b) converting 3,3,5,5-tetramethylcyclohexanone 1,3,3,5,5-pentamethylcyclohexanol:
(c) converting 1,3,3,5,5-pentamethylcyclohexanol to 1-amino-1,3,3,5,5-pentamethylcyclohexane.

18. The process according to any one of claims 1 to 17, further comprising step (vii):
(vii) converting 1-amino-1,3,3,5,5-pentamethylcyclohexane mesylate obtained according to any one of the preceding claims to 1-amino-1,3,3,5,5-pentamethylcyclohexane.

19. A process for the crystallization and/or re-crystallization of 1-amino-1,3,3,5,5-pentamethylcyclohexane mesylate comprising reacting a mixture of 1-amino-1,3,3,5,5-pentamethylcyclohexane and methane sulfonic acid and/or 1-amino-1,3,3,5,5-pentamethylcyclohexane mesylate with anisole as a solvent or a solvent mixture of anisole and at least one additional solvent selected from the group consisting of cumene, pentane, hexane, heptane, isooctane, methyl acetate, propyl acetate, isopropyl acetate, n-butyl acetate, isobutyl acetate, methyl ethyl ketone, methyl isopropylketone, methyl isobutyl ketone, dimethyl sulphoxide, tetrahydrofuran, methyltetrahydrofuran, 1,1-diethoxypropane, 1,1-dimethoxymethane, and 2,2-dimethoxypropane to form a reaction mixture; allowing the reaction to proceed, and reducing the temperature of the reaction mixture to obtain the crystallized and/or re-crystallized 1-amino-1,3,3,5,5-pentamethylcyclohexane mesylate.

20. The process according to claim 5, wherein the solvent includes from 0.1 to 8% by weight water based on the total amount of water and solvent.

21. The process according to claim 5, wherein the solvent includes from 0.1 to 5% by weight water based on the total amount of water and solvent.

22. The process according to claim 5, wherein the solvent includes from 0.1 to 4% by weight water based on the total amount of water and solvent.

23. The process according to claim 5, wherein the solvent includes from 0.1 to 2% by weight water based on the total amount of water and solvent.

24. The process according to claim 5, wherein the solvent includes from 0.1 to 1% by weight water based on the total amount of water and solvent.

* * * * *

UNITED STATES PATENT AND TRADEMARK OFFICE
CERTIFICATE OF CORRECTION

PATENT NO. : 8,784,847 B2  
APPLICATION NO. : 13/138883  
DATED : July 22, 2014  
INVENTOR(S) : Markus Henrich et al.

Page 1 of 1

It is certified that error appears in the above-identified patent and that said Letters Patent is hereby corrected as shown below:

In the Claims

Claim 18, Column 36, Line 26: "(vii)" should be --(vi)--.

Claim 18, Column 36, Line 27: "(vii)" should be --(vi)--.

Signed and Sealed this
Fourth Day of November, 2014

Michelle K. Lee
*Deputy Director of the United States Patent and Trademark Office*